US008133723B2

(12) United States Patent
Draghia-Akli et al.

(10) Patent No.: US 8,133,723 B2
(45) Date of Patent: Mar. 13, 2012

(54) VACCINES AGAINST MULTIPLE SUBTYPES OF INFLUENZA VIRUS

(75) Inventors: Ruxandra Draghia-Akli, Brussels (BE); David B Weiner, Merion, PA (US); Jian Yan, Havertown, PA (US); Dominick J Laddy, Germantown, MD (US)

(73) Assignee: The Trustees of The University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/158,150

(22) Filed: Jun. 10, 2011

(65) Prior Publication Data
US 2011/0305664 A1 Dec. 15, 2011

Related U.S. Application Data

(62) Division of application No. 12/269,824, filed on Nov. 12, 2008.

(60) Provisional application No. 60/987,284, filed on Nov. 12, 2007.

(51) Int. Cl.
*C12N 15/00* (2006.01)
*C12P 21/06* (2006.01)
*A61K 39/145* (2006.01)
*C07H 21/02* (2006.01)

(52) U.S. Cl. ............ 435/320.1; 435/69.1; 435/7.1; 424/206.1; 536/23.1

(58) Field of Classification Search .................. None
See application file for complete search history.

(56) References Cited

U.S. PATENT DOCUMENTS

| | | | |
|---|---|---|---|
| 5,593,972 | A | 1/1997 | Weiner et al. |
| 5,908,780 | A | 6/1999 | Jones |
| 5,962,428 | A | 10/1999 | Carrano et al. |
| 7,238,522 | B2 | 7/2007 | Hebel et al. |
| 7,245,963 | B2 | 7/2007 | Draghia-Akli et al. |
| 7,262,045 | B2 | 8/2007 | Schwartz et al. |
| 2004/0175727 | A1 | 9/2004 | Draghia-Akli et al. |
| 2005/0052630 | A1 | 3/2005 | Smith et al. |
| 2006/0024670 | A1 | 2/2006 | Luke et al. |
| 2006/0165684 | A1 | 7/2006 | Utku |
| 2008/0091135 | A1 | 4/2008 | Draghia-Akli |

FOREIGN PATENT DOCUMENTS

| | | |
|---|---|---|
| WO | WO9324640 | 12/1993 |
| WO | WO9416737 | 8/1994 |
| WO | 2007011904 | 1/2007 |
| WO | 2008091657 | 7/2008 |
| WO | 2008124331 | 10/2008 |

OTHER PUBLICATIONS

Stobie, L. et al., "The role of antigen and IL-12 in sustaining Th1 memory cells in vivo: IL-12 is required to maintain memory/effector Th1 cells sufficient to mediate protection to an infectious parasite challenge", PNAS, 2000, 97:8427-8432.
Soh J-W et al., "Novel roles of specific isoforms of protein kinase C in activation of the c-fos serum response element", Molecular and Cell Biology, 1999, 19:1313-1324.
Wong et al., "DNA vaccination against respiratory influenza virus infection", Vaccine, 2001, 19:2461-2467.
Nicol, F. et al., "Poly-L-glutamate, an anionic polymer, enhances transgene expression for plasmids delivered by intramuscular injection with an in vivo electroporation", Gene Therapy, 2002, 9:1351-1358.
Altschul et al., "Gapped BLAST and PSI-BLAST: a new generation of protein database search programs", Nuc. Acids Res., 1997, 25:3389-3402.
Altschul et al., "Basic local alignment search tool", J. Mol. Biol., 1990, 215:403-410.
Holland, D. et al., "Intradermal influenza vaccine administered using a new microinjection system produces superior immunogenicity in elderly adults: a randomized controlled trial", J Inf Dis, 2008, 198:650-658.
Gronevik, E. et al., "Gene expression and immune response kinetics using electroporation-mediated DNA delivery to muscle", J Gene Med, 2005, 7(2)218-227.

*Primary Examiner* — Bo Peng
(74) *Attorney, Agent, or Firm* — Pepper Hamilton LLP

(57) ABSTRACT

An aspect of the present invention is directed towards DNA plasmid vaccines capable of generating in a mammal an immune response against a plurality of influenza virus subtypes, comprising a DNA plasmid and a pharmaceutically acceptable excipient. The DNA plasmid is capable of expressing a consensus influenza antigen in a cell of the mammal in a quantity effective to elicit an immune response in the mammal, wherein the consensus influenza antigen comprises consensus hemagglutinin (HA), neuraminidase (NA), matrix protein, nucleoprotein, M2 ectodomain-nucleoprotein (M2e-NP), or a combination thereof. Preferably the consensus influenza antigen comprises HA, NA, M2e-NP, or a combination thereof. The DNA plasmid comprises a promoter operably linked to a coding sequence that encodes the consensus influenza antigen. Additionally, an aspect of the present invention includes methods of eliciting an immune response against a plurality of influenza virus subtypes in a mammal using the DNA plasmid vaccines provided.

52 Claims, 5 Drawing Sheets

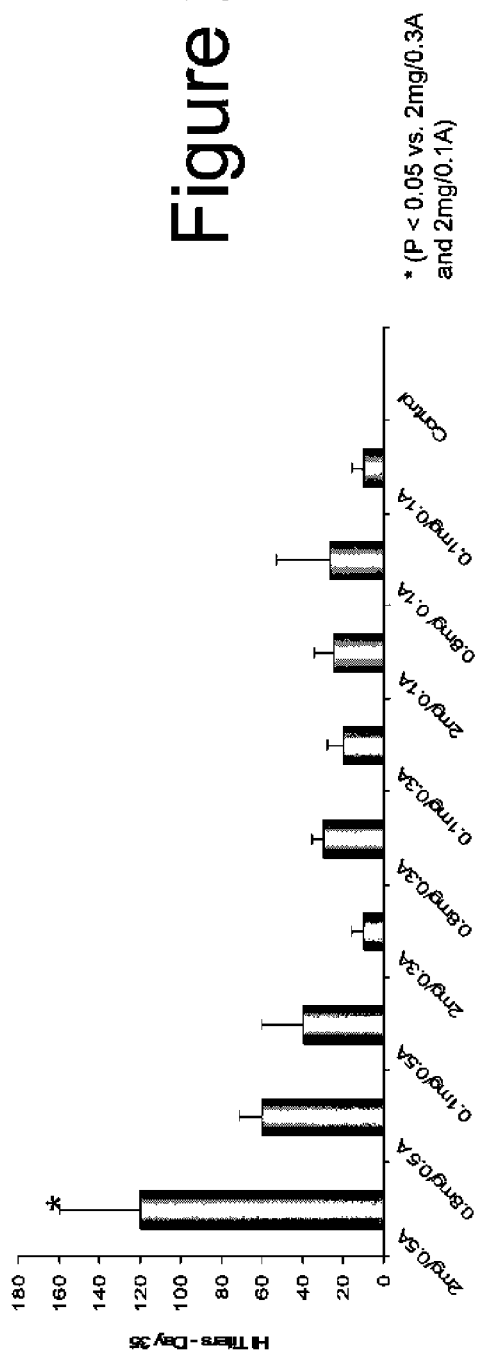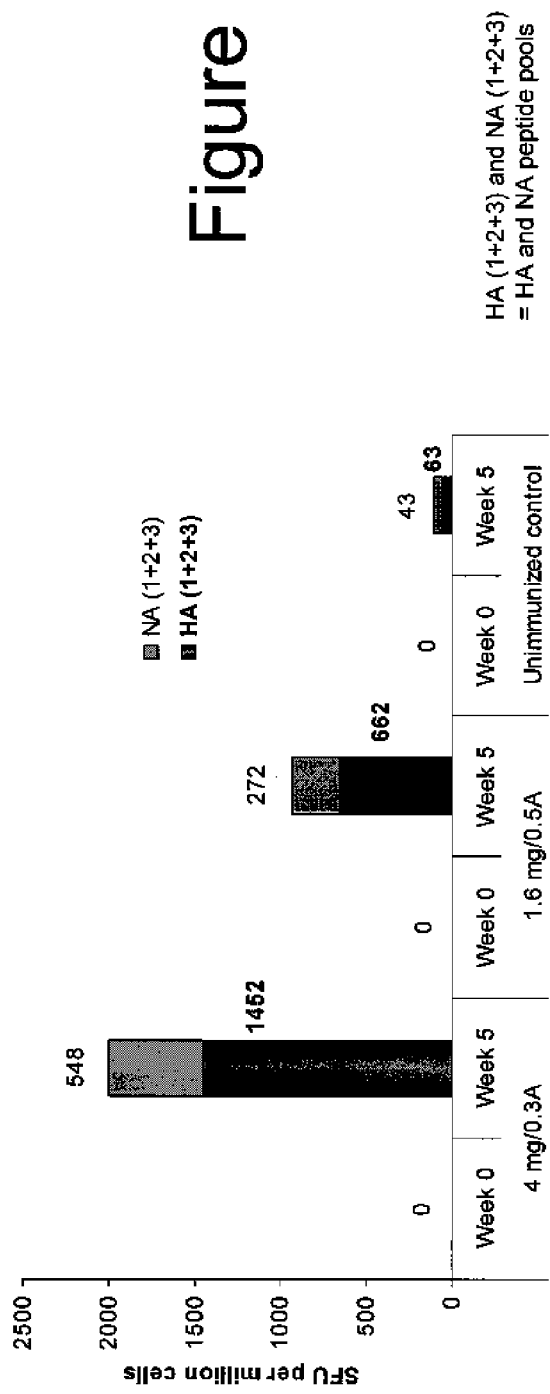

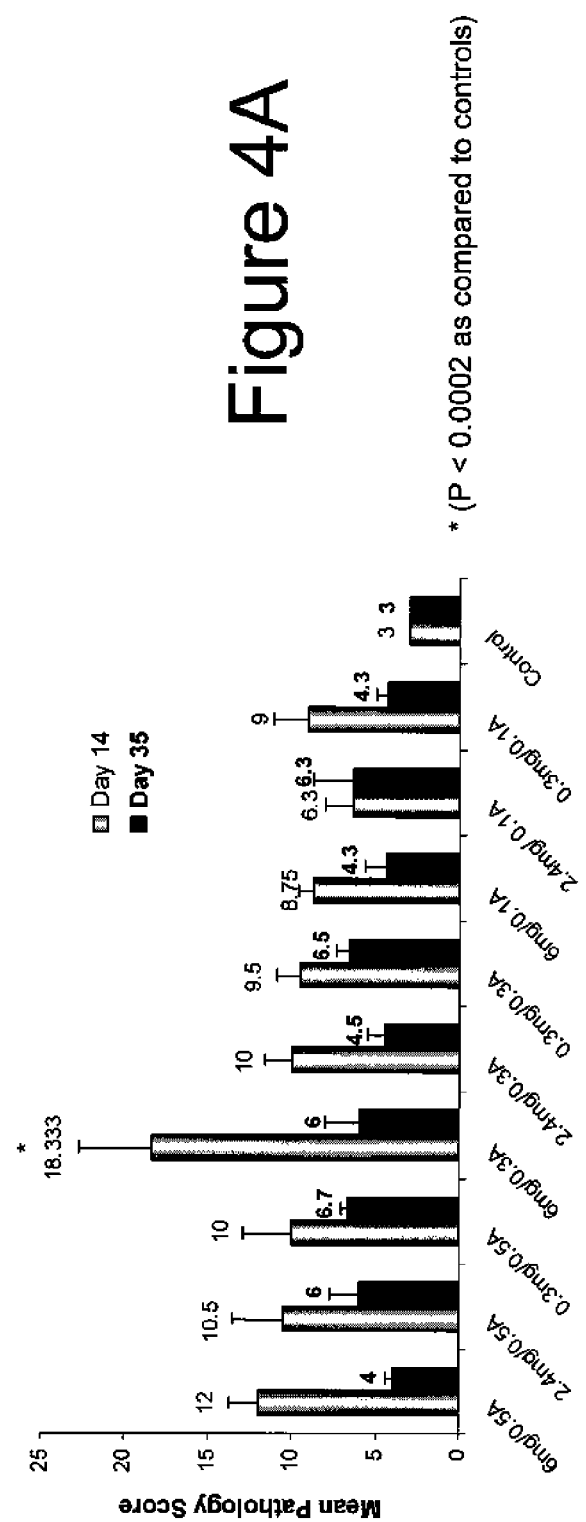
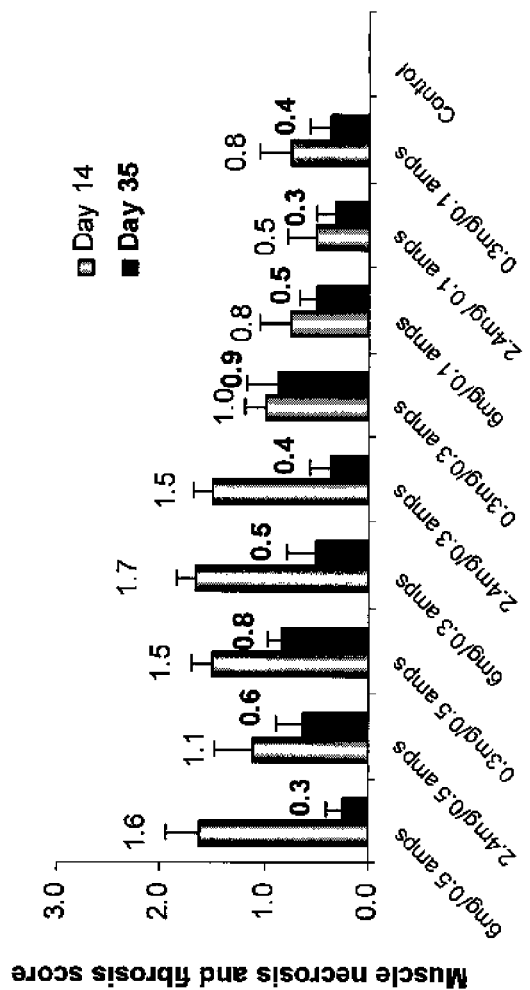

VACCINES AGAINST MULTIPLE SUBTYPES OF INFLUENZA VIRUS

CROSS REFERENCE TO RELATED APPLICATIONS

This application is a divisional of U.S. patent application Ser. No. 12/269,824, filed Nov. 12, 2008, pending, which claims the benefit of U.S. Provisional Application No. 60/987,284, filed Nov. 12, 2007, the contents of which are incorporated herein by reference.

FIELD OF THE INVENTION

The present invention relates to improved influenza vaccines, improved methods for inducing immune responses, and for prophylactically and/or therapeutically immunizing individuals against influenza.

BACKGROUND

The use of nucleic acid sequences to vaccinate against animal and human diseases has been studied. Studies have focused on effective and efficient means of delivery in order to yield necessary expression of the desired antigens, resulting immunogenic response and ultimately the success of this technique. One method for delivering nucleic acid sequences such as plasmid DNA is the electroporation (EP) technique. The technique has been used in human clinical trials to deliver anti-cancer drugs, such as bleomycin, and in many preclinical studies on a large number of animal species.

The influenza virus genome is contained on eight single (non-paired) RNA strands that code for eleven proteins (HA, NA, NP, M1, M2, NS1, NEP, PA, PB1, PB1-F2, PB2). The segmented nature of the genome allows for the exchange of entire genes between different viral strains during cellular cohabitation. The eight RNA segments are: HA, which encodes hemagglutinin (about 500 molecules of hemagglutinin are needed to make one virion); NA, which encodes neuraminidase (about 100 molecules of neuraminidase are needed to make one virion); NP, which encodes nucleoprotein; M, which encodes two matrix proteins (the M1 and the M2) by using different reading frames from the same RNA segment (about 3000 matrix protein molecules are needed to make one virion); NS, which encodes two distinct non-structural proteins (NS1 and NEP) by using different reading frames from the same RNA segment; PA, which encodes an RNA polymerase; PB1, which encodes an RNA polymerase and PB1-F2 protein (induces apoptosis) by using different reading frames from the same RNA segment; and PB2, which encodes an RNA polymerase.

Influenza hemagglutinin (HA) is expressed on the surface of influenza viral particles and is responsible for initial contact between the virus and its host cell. HA is a well-known immunogen. Influenza A strain H5N1, an avian influenza strain, particularly threatens the human population because of its HA protein (H5) which, if slightly genetically reassorted by natural mutation, has greatly increased infectivity of human cells as compared to other strains of the virus. Infection of infants and older or immunocompromised adult humans with the viral H5N1 strain is often correlated to poor clinical outcome. Therefore, protection against the H5N1 strain of influenza is a great need for the public.

There are two classes of anti-influenza agents available, inhibitors of influenza A cell entry/uncoating (such as antivirals amantadine and rimantadine) and neuraminidase inhibitors (such as antivirals oseltamivir, zanamivir). These antiviral agents inhibit the cellular release of both influenza A and B. Concerns over the use of these agents have been reported due to findings of strains of virus resistant to these agents.

Influenza vaccines are a popular seasonal vaccine and many people have experienced such vaccinations. However, the vaccinations are limited in their protective results because the vaccines are specific for certain subtypes of virus. The Centers for Disease Control and Prevention promote vaccination with a "flu shot" that is a vaccine that contains three influenza viruses (killed viruses): one A (H3N2) virus, one A (H1N1) virus, and one B virus. They also report that the viruses in the vaccine change each year based on international surveillance and scientists' estimations about which types and strains of viruses will circulate in a given year. Thus, it is apparent that vaccinations are limited to predictions of subtypes, and the availability of a specific vaccine to that subtype.

There still remains a need for effective influenza vaccines that are economical and effective across numerous subtypes. Further, there remains a need for an effective method of administering DNA vaccines to a mammal in order to provide immunization against influenza either prophylactically or therapeutically.

SUMMARY OF THE INVENTION

One aspect of the present invention relates to a DNA plasmid vaccine capable of generating in a mammal an immune response against a plurality of influenza virus subtypes, comprising a DNA plasmid and a pharmaceutically acceptable excipient. The DNA plasmid is capable of expressing a consensus influenza antigen in a cell of the mammal in a quantity effective to elicit an immune response in the mammal, wherein the consensus influenza antigen comprises consensus hemagglutinin (HA), neuraminidase (NA), matrix protein, nucleoprotein, M2 ectodomain-nucleo-protein (M2e-NP), or a combination thereof. Preferably the consensus influenza antigen comprises HA, NA, M2e-NP, or a combination thereof. The DNA plasmid comprises a promoter operably linked to a coding sequence that encodes the consensus influenza antigen. Preferably, the DNA plasmid vaccine is one having a concentration of total DNA plasmid of 1 mg/ml or greater.

Another aspect of the present invention relates to DNA plasmids capable of expressing a consensus influenza antigen in a cell of the mammal, the consensus influenza antigen comprising consensus hemagglutinin (HA), neuraminidase (NA), matrix protein, nucleoprotein, M2 ectodomain-nucleo-protein (M2e-NP), or a combination thereof. Preferably the consensus influenza antigen comprises HA, NA, M2e-NP, or a combination thereof. The DNA plasmid comprises a promoter operably linked to a coding sequence that encodes the consensus influenza antigen.

Another aspect of the present invention relates to methods of eliciting an immune response against a plurality of influenza virus subtypes in a mammal. The methods include delivering a DNA plasmid vaccine to tissue of the mammal, the DNA plasmid vaccine comprising a DNA plasmid capable of expressing a consensus influenza antigen in a cell of the mammal to elicit an immune response in the mammal, the consensus influenza antigen comprising consensus HA, NA, M2e-NP or a combination thereof, and electroporating cells of the tissue with a pulse of energy at a constant current effective to permit entry of the DNA plasmids in the cells.

BRIEF DESCRIPTION OF THE DRAWINGS

The numerous objects and advantages of the present invention may be better understood by those skilled in the art by reference to the accompanying figures, in which.

Figure 1:
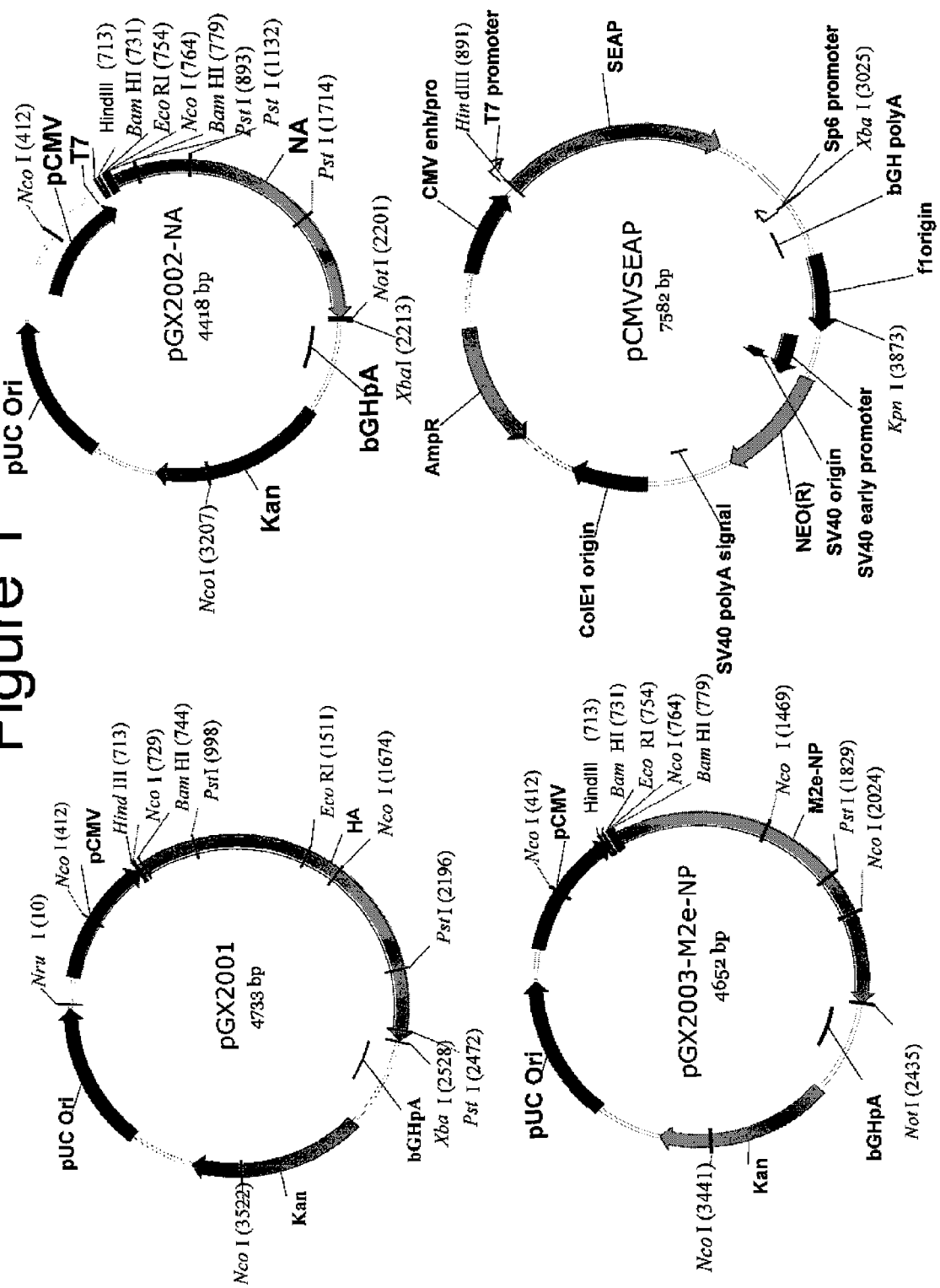
FIG. 1 displays a schematic representation (plasmid maps) of the DNA plasmid constructs used in the studies described herein. Consensus HA, NA and M2e-NP constructs were generated by analyzing primary virus sequences from 16 H5 viruses that have proven fatal to humans in recent years, and over 40 human N1 viruses (Los Alamos National Laboratory's Influenza Sequence Database). After generating the consensus sequences, the constructs were optimized for mammalian expression, including the addition of a Kozak sequence, codon optimization, and RNA optimization. These constructs were then subcloned into the pVAX vector (Invitrogen, Carlsbad, Calif.). Plasmids pGX2001 (consensus HA), pGX2002 (consensus NA), pGX2003 (consensus M2e-NP) are shown. The plasmid pCMVSEAP, displayed, encodes the reporter protein secreted embryonic alkaline phosphatase (SEAP).

FIG. 2 displays a bar graph of the results of the HI titers in pig serum at Day 35 post-injection. The highest titers were found in the group administered 2 mg of HA-expressing plasmid at a current setting of 0.5 A (120±40; *P=0.11 versus 2 mg/0.3 A and *P=0.02 versus 2 mg/0.1 A). The three groups administered descending doses of plasmid and electroporated at 0.5 A also demonstrated decreasing HI titers.

FIG. 3 displays a bar graph of the IFN-γ ELISpot counts. The counts were highest in pigs administered 2 mg of HA and 2 mg of NA plasmid vaccine (for a total of 4 mg plasmid) and electroporated with 0.3 A of current (2000 spots) and in the group administered 0.8 mg of HA and 0.8 mg of NA plasmid vaccine (for a total of 1.6 mg plasmid) electroporated with 0.5 A of current (934 spots). For comparison purposes, the cellular immune responses of an unimmunized control group are depicted.

FIGS. 4A and 4B display bar graphs showing results from muscle biopsies from treated pigs at Day 14 and Day 35: FIG. 4A displays a bar graph showing the mean pathology scores for all groups. FIG. 4B displays a bar graph showing the muscle necrosis and fibrosis scores. The group injected with 6 mg total plasmid and electroporated at 0.5 A exhibited the highest mean pathology score (*P<0.0002 as compared to controls). The pathology scores were significantly reduced by Day 35 compared to Day 14 in all groups (P<0.05) except for the 0.3 mg/0.3 A group (P=0.057) and 2.4 mg/0.1 A group (P=1.0).

FIG. 5 displays the percent change in weight of ferrets after challenge with H5N1 virus (A/Viet/1203/2004(H5N1)/PR8-IBCDC-RG). Ferrets that were vaccinated with HA, HA+M2e-NP or HA+M2e-NP+NA lost significantly less weight than control animals (*P<0.005 versus controls) in the 9 days post-challenge period. One animal in the HA vaccine group actually gained weight post-challenge.

FIG. 6 displays a graph showing the body temperatures of ferrets during the 9 days post-challenge. Control animals showed higher body temperatures than the vaccinated animals. The body temperature on day 5 is not depicted as it was measured at a different time of day and all the temperatures regardless of group were lower.

FIG. 7 displays a bar graph of results from HI titers in ferrets after vaccination; the assay was performed using reassortant viruses obtained from the Center for Disease Control: A/Viet/1203/04 or Indo/05/2005 influenza strains.

FIG. 8 displays a bar graph of results from HI titers measured three weeks after the second immunization. Macaques immunized ID followed by EP showed significantly higher HI titers than all other groups (P<0.03). Non-treated controls did not exhibit any HI titers.

DETAILED DESCRIPTION OF PREFERRED EMBODIMENTS

The following abbreviated, or shortened, definitions are given to help the understanding of the preferred embodiments of the present invention. The abbreviated definitions given here are by no means exhaustive nor are they contradictory to the definitions as understood in the field or dictionary meaning. The abbreviated definitions are given here to supplement or more clearly define the definitions known in the art.

Definitions

Sequence homology for nucleotides and amino acids as used herein may be determined using FASTA, BLAST and Gapped BLAST (Altschul et al., Nuc. Acids Res., 1997, 25, 3389, which is incorporated herein by reference in its entirety) and PAUP* 4.0b10 software (D. L. Swofford, Sinauer Associates, Massachusetts). Briefly, the BLAST algorithm, which stands for Basic Local Alignment Search Tool is suitable for determining sequence similarity (Altschul et al., J. Mol. Biol., 1990, 215, 403-410, which is incorporated herein by reference in its entirety). Software for performing BLAST analyses is publicly available through the National Center for Biotechnology Information (http://www.ncbi.nlm.nih.gov). One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, preferably less than about 0.1, more preferably less than about 0.01, and most preferably less than about 0.001. "Percentage of similarity" can be calculated using PAUP* 4.0b10 software (D. L. Swofford, Sinauer Associates, Massachusetts). The average similarity of the consensus sequence is calculated compared to all sequences in the phylogenic tree.

As used herein, the term "genetic construct" or "nucleic acid construct" is used interchangeably and refers to the DNA or RNA molecules that comprise a nucleotide sequence which encodes protein. The coding sequence, or "encoding nucleic acid sequence," includes initiation and termination signals operably linked to regulatory elements including a promoter and polyadenylation signal capable of directing expression in the cells of the individual to whom the nucleic acid molecule is administered.

As used herein, the term "expressible form" refers to nucleic acid constructs that contain the necessary regulatory elements operable linked to a coding sequence that encodes a protein such that when present in the cell of the individual, the coding sequence will be expressed.

The term "constant current" is used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

The term "feedback" or "current feedback" is used interchangeably and means the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. Preferably, the feedback is accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. In some embodiments, the feedback loop is instantaneous as it is an analog closed-loop feedback.
Figure 5:
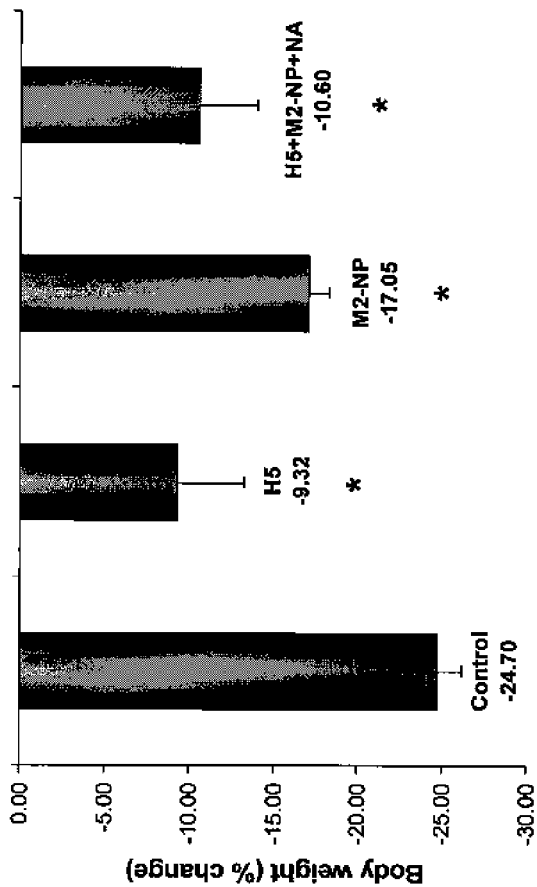

The terms "electroporation," "electro-permeabilization," or "electro-kinetic enhancement" ("EP") as used interchangeably herein refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

The term "decentralized current" is used herein to define the pattern of electrical currents delivered from the various needle electrode arrays of the electroporation devices described herein, wherein the patterns minimize, or preferably eliminate, the occurrence of electroporation related heat stress on any area of tissue being electroporated.

The term "feedback mechanism" as used herein refers to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. The term "impedance" is used herein when discussing the feedback mechanism and can be converted to a current value according to Ohm's law, thus enabling comparisons with the preset current. In a preferred embodiment, the "feedback mechanism" is performed by an analog closed loop circuit.

The term "immune response" is used herein to mean the activation of a host's immune system, e.g., that of a mammal, in response to the introduction of influenza consensus antigen via the provided DNA plasmid vaccines. The immune response can be in the form of a cellular or humoral response, or both.

The term "consensus" or "consensus sequence" is used herein to mean a synthetic nucleic acid sequence, or corresponding polypeptide sequence, constructed based on analysis of an alignment of multiple subtypes of a particular influenza antigen, that can be used to induce broad immunity against multiple subtypes or serotypes of a particular influenza antigen. Consensus influenza antigens include HA, including consensus H1, H2, H3, or H5, NA, NP, matrix protein, and nonstructural protein. Also, synthetic antigens such as fusion proteins, e.g., M2e-NP, can be manipulated to consensus sequences (or consensus antigens).

The term "adjuvant" is used herein to mean any molecule added to the DNA plasmid vaccines described herein to enhance antigenicity of the influenza antigen encoded by the DNA plasmids and encoding nucleic acid sequences described hereinafter.

The term "subtype" or "serotype" is used herein interchangeably and in reference to influenza viruses, and means genetic variants of an influenza virus antigen such that one subtype is recognized by an immune system apart from a different subtype (or, in other words, each subtype is different in antigenic character from a different subtype).

In some embodiments, there are DNA plasmids capable of expressing a consensus influenza antigen in a cell of the mammal, the consensus influenza antigen comprising consensus hemagglutinin (HA), neuraminidase (NA), matrix protein, nucleoprotein, M2 ectodomain-nucleo-protein (M2e-NP), or a combination thereof. Preferably the consensus influenza antigen comprises HA, NA, M2e-NP, or a combination thereof. The DNA plasmid comprises a promoter operably linked to a coding sequence that encodes the consensus influenza antigen.

In some embodiments, the present invention provides DNA plasmid vaccines that are capable of generating in a mammal an immune response against a plurality of influenza virus subtypes, the DNA plasmid vaccines comprising a DNA plasmid and a pharmaceutically acceptable excipient. The DNA plasmid is capable of expressing a consensus influenza antigen in a cell of the mammal in a quantity effective to elicit an immune response in the mammal, wherein the consensus influenza antigen comprises consensus hemagglutinin (HA), neuraminidase (NA), matrix protein, nucleoprotein, M2 ectodomain-nucleo-protein (M2e-NP), or a combination thereof. Preferably the consensus influenza antigen comprises HA, NA, M2e-NP, or a combination thereof. The DNA plasmid comprises a promoter operably linked to a coding sequence that encodes the consensus influenza antigen. In some embodiments, the DNA plasmid vaccine is one having a concentration of total DNA plasmid of 1 mg/ml or greater. The immune response can be a cellular or humoral response, or both; preferably, the immune response is both cellular and humoral.

In some embodiments, the DNA plasmid can further include an IgG leader sequence attached to an N-terminal end of the coding sequence and operably linked to the promoter. In addition, in some embodiments, the DNA plasmid can further include a polyadenylation sequence attached to the C-terminal end of the coding sequence. In some embodiments, the DNA plasmid is codon optimized.

In some embodiments of the present invention, the DNA plasmid vaccines can further include an adjuvant. In some embodiments, the adjuvant is selected from the group consisting of: alpha-interferon, gamma-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. Other genes which may be useful adjuvants include those encoding: MCP-1, MIP-1α, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof. In some preferred embodiments, the adjuvant is selected from IL-12, IL-15, CTACK, TECK, or MEC.

In some embodiments, the pharmaceutically acceptable excipient is a transfection facilitating agent, which can include the following: surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents. Preferably, the transfection facilitating agent is a polyanion, polycation, including poly-L-glutamate (LGS), or lipid. Preferably, the transfection facilitating agent is poly-L-glutamate, and more preferably, the poly-L-glutamate is present in the DNA plasmid vaccine at a concentration less than 6 mg/ml. In some embodiments, the concentration of poly-L-glutamate in the DNA plasmid vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

In some embodiments, the DNA plasmid vaccine can include a plurality of different DNA plasmids. In some examples, the different DNA plasmids include a DNA plasmid comprising a nucleic acid sequence that encodes a consensus HA, a DNA plasmid comprising a sequence that encodes a consensus NA, and a DNA plasmid comprising a sequence that encodes a consensus M2e-NP. In some embodiments, the consensus HA is a consensus H1, consensus H2, consensus H3, or consensus H5. Preferably, the consensus HA is nucleotide sequence that is SEQ ID NO:1 (H5N1 HA consensus DNA), SEQ ID NO:9 (consensus H1 DNA), SEQ ID NO: 11 (consensus H3 DNA), or SEQ ID NO:13 (consensus H5). The consensus HA can also be a nucleotide sequence encoding a polypeptide of the sequence SEQ ID NO: 2, SEQ ID NO: 10, SEQ ID NO: 12, or SEQ ID NO:14. In some embodiments, the consensus NA is a nucleotide sequence that is SEQ ID NO: 3, or a nucleotide sequence encoding a polypeptide of the sequence SEQ ID NO: 4. In some embodiments, the consensus M2e-NP is a nucleotide sequence that is SEQ ID NO:7, or a nucleotide sequence encoding a polypeptide of the sequence SEQ ID NO:8. In one preferred embodiment, the DNA plasmid vaccine includes a DNA plasmid comprising a sequence that encodes a consensus H1, a DNA plasmid comprising a sequence that encodes a consensus H2, a DNA plasmid comprising a sequence that encodes a consensus H3, a DNA plasmid comprising a sequence that encodes a consensus H5, a DNA plasmid comprising a sequence that encodes a consensus NA, and a DNA plasmid comprising a sequence that encodes a consensus M2e-NP.

In some embodiments, the DNA plasmid vaccine can include a plurality of different DNA plasmids, including at least one DNA plasmid that can express consensus influenza antigens and at least one that can express one influenza subtype antigen. In some examples, the different DNA plasmids that express consensus antigen include a DNA plasmid comprising a nucleic acid sequence that encodes a consensus HA, a DNA plasmid comprising a sequence that encodes a consensus NA, and a DNA plasmid comprising a sequence that encodes a consensus M2e-NP. In some embodiments, the DNA plasmid vaccine comprises a DNA plasmid that can express a consensus HA antigen, e.g., consensus H1, H3 or H5, and a DNA plasmid that can express any one of the following influenza A antigens: H1, H2, H3, H4, H5, H6, H7, H8, H9, H10, H11, H12, H13, H14, H15, H16, N1, N2, N3, N4, N5, N6, N7, N8, N9, NP, M1, M2, NS1, or NEP, or a combination thereof. In some embodiments, the DNA plasmid vaccine comprises a DNA plasmid that can express a consensus NA antigen and a DNA plasmid that can express any one of the following influenza A antigens: H1, H2, H3, H4, H5, H6, H7, H8, H9, H10, H11, H12, H13, H14, H15, H16, N1, N2, N3, N4, N5, N6, N7, N8, N9, NP, M1, M2, NS1, or NEP, or a combination thereof. In some embodiments, the DNA plasmid vaccine comprises a DNA plasmid that can express a consensus M2e-NP and a DNA plasmid that can express any one of the following influenza A antigens: H1, H2, H3, H4, H5, H6, H7, H8, H9, H10, H11, H12, H13, H14, H15, H16, N1, N2, N3, N4, N5, N6, N7, N8, N9, NP, M1, M2, NS1, or NEP, or a combination thereof.

In some embodiments, the DNA plasmid vaccine can be delivered to a mammal to elicit an immune response; preferably the mammal is a primate, including human and nonhuman primate, a cow, pig, chicken, dog, or ferret. More preferably, the mammal is a human primate.

One aspect of the present invention relates to methods of eliciting an immune response against a plurality of influenza virus subtypes in a mammal. The methods include delivering a DNA plasmid vaccine to tissue of the mammal, the DNA plasmid vaccine comprising a DNA plasmid capable of expressing a consensus influenza antigen in a cell of the mammal to elicit an immune response in the mammal, the consensus influenza antigen comprising consensus HA, NA, M2e-NP or a combination thereof, and electroporating cells of the tissue with a pulse of energy at a constant current effective to permit entry of the DNA plasmids in the cells.

In some embodiments, the methods of the present invention include the delivering step, which comprises injecting the DNA plasmid vaccine into intradermic, subcutaneous or muscle tissue. Preferably, these methods include using an in vivo electroporation device to preset a current that is desired to be delivered to the tissue; and electroporating cells of the tissue with a pulse of energy at a constant current that equals the preset current. In some embodiments, the electroporating step further comprises: measuring the impedance in the electroporated cells; adjusting energy level of the pulse of energy relative to the measured impedance to maintain a constant current in the electroporated cells; wherein the measuring and adjusting steps occur within a lifetime of the pulse of energy.

In some embodiments, the electroporating step comprises delivering the pulse of energy to a plurality of electrodes according to a pulse sequence pattern that delivers the pulse of energy in a decentralized pattern.

In some embodiments, the DNA plasmid influenza vaccines of the invention comprise nucleotide sequences that encode a consensus HA, or a consensus HA and a nucleic acid sequence encoding influenza proteins selected from the group consisting of: SEQ ID NOS: 4, 6, and 8. SEQ ID NOS: 1 and 13 comprise the nucleic acid sequence that encodes consensus H5N1 HA and H5 of influenza virus, respectively. SEQ ID NOS: 2 and 14 comprise the amino acid sequence for H5N1 HA and H5 of influenza virus, respectively. In some embodiments of the invention, the vaccines of the invention comprise SEQ ID NO:3 or SEQ ID NO:4. SEQ ID NO:3 comprises the nucleic acid sequence that encodes influenza H1N1 and H5N1 (H1N1/H5N1) NA consensus sequences. SEQ ID NO:4 comprises the amino acid sequence for influenza H1N1/H5N1 NA consensus sequences. In some embodiments of the invention, the vaccines of the invention comprise SEQ ID NO:5 or SEQ ID NO:6. SEQ ID NO:5 comprises the nucleic acid sequence that encodes influenza H1N1/H5N1 M1 consensus sequences. SEQ ID NO:6 comprises the amino acid sequence for influenza H1N1/H5N1 M1 consensus sequences. In some embodiments of the invention, the vaccines of the invention comprise SEQ ID NO:7 or SEQ ID NO:8. SEQ ID NO:7 comprises the nucleic acid sequence that encodes influenza H5N1 M2E-NP consensus sequence. SEQ ID NO:8 comprises the amino acid sequence for influenza H5N1 M2E-NP consensus sequence. In some embodiments of the invention, the vaccines of the invention comprise SEQ ID NO:9 or SEQ ID NO:10. SEQ ID NO:9 comprises the nucleic acid sequence that encodes influenza H1N1 HA consensus sequences. SEQ ID NO:4 comprises the amino acid sequence for influenza H1N1 HA consensus sequences. In some embodiments of the invention, the vaccines of the invention comprise SEQ ID NO:11 or SEQ ID NO:12. SEQ ID NO:11 comprises the nucleic acid sequence that encodes influenza H3N1 HA consensus sequences. SEQ ID NO:12 comprises the amino acid sequence for influenza H3N1 HA consensus sequences. The consensus sequence for influenza virus strain H5N1 HA includes the immunodominant epitope set forth in SEQ ID NO:1 or SEQ ID NO:13. The influenza virus H5N1 HA amino acid sequence encoded by SEQ ID NO:1 is SEQ ID NO:2, and that encoded by SEQ ID NO:13 is SEQ ID NO:14. The consensus sequence for influenza virus H1N1/H5N1 NA includes the immunodominant epitope set forth in SEQ ID NO:3. The influenza virus strains H1N1/H5N1 NA amino acid sequence encoded by SEQ ID NO:3 is SEQ ID NO:4. The consensus sequence for influenza virus strains H1N1/H5N1 M1 includes the immunodominant epitope set forth in SEQ ID NO:5. The influenza virus H1N1/H5N1 M1 amino acid sequence encoded by SEQ ID NO:5 is SEQ ID NO:6. The consensus sequence for influenza virus H5N1 M2E-NP includes the immunodominant epitope set forth in SEQ ID NO:7. The influenza virus H5N1 M2E-NP amino acid sequence encoded by SEQ ID NO:7 is SEQ ID NO:8. Vaccines of the present invention may include protein products encoded by the nucleic acid molecules defined above or any fragments of proteins.

The present invention also comprises DNA fragments that encode a polypeptide capable of eliciting an immune response in a mammal substantially similar to that of the non-fragment for at least one influenza subtype. The DNA fragments are fragments selected from at least one of the various encoding nucleotide sequences of the present invention, including SEQ ID NOS: 1, 3, 5, 7, 9, 11, and 13, and can be any of the following described DNA fragments, as it applies to the specific encoding nucleic acid sequence provided herein. In some embodiments, DNA fragments can comprise 30 or more, 45 or more, 60 or more, 75 or more, 90 or more, 120 or more, 150 or more, 180 or more, 210 or more, 240 or more, 270 or more, 300 or more, 360 or more, 420 or more, 480 or more, 540 or more, 600 or more, 660 or more, 720 or more, 780 or more, 840 or more, 900 or more, 960 or more, 1020 or more, 1080 or more, 1140 or more, 1200 or more, 1260 or more, 1320 or more, 1380 or more, 1440 or more, 1500 or more, 1560 or more, 1620 or more, 1680 or more, or 1740 or more nucleotides. In some embodiments, DNA fragments can comprise coding sequences for the immunoglobulin E (IgE) leader sequences. In some embodiments, DNA fragments can comprise fewer than 60, fewer than 75, fewer than 90, fewer than 120, fewer than 150, fewer than 180, fewer than 210, fewer than 240, fewer than 270, fewer than 300, fewer than 360, fewer than 420, fewer than 480, fewer than 540, fewer than 600, fewer than 660, fewer than 720, fewer than 780, fewer than 840, fewer than 900, fewer than 960, fewer than 1020, fewer than 1080, fewer than 1140, fewer than 1200, fewer than 1260, fewer than 1320, fewer than 1380, fewer than 1440, fewer than 1500, fewer than 1560, fewer than 1620, fewer than 1680, or fewer than 1740 nucleotides. Preferably, the DNA fragments are fragments of SEQ ID NOS:1, 3, 7, 9, 11 or 13, and more preferably fragments of SEQ ID NOS:1, 5, 9, 11, or 13, and even more preferably fragments of SEQ ID NOS:1, 9, or 13.

The present invention also comprises polypeptide fragments that are capable of eliciting an immune response in a mammal substantially similar to that of the non-fragment for at least one influenza subtype. The polypeptide fragments are selected from at least one of the various polypeptide sequences of the present invention, including SEQ ID NOS:2, 4, 6, 8, 10, 12, and 14, and can be any of the following described polypeptide fragments, as it applies to the specific polypeptide sequence provided herein. In some embodiments, polypeptide fragments can comprise 15 or more, 30 or more, 45 or more, 60 or more, 75 or more, 90 or more, 105 or more, 120 or more, 150 or more, 180 or more, 210 or more, 240 or more, 270 or more, 300 or more, 360 or more, 420 or more, 480 or more, 540 or more, or 565 or more amino acids. In some embodiments, polypeptide fragments can comprise fewer than 30, fewer than 45, fewer than 60, fewer than 75, fewer than 90, fewer than 120, fewer than 150, fewer than 180, fewer than 210, fewer than 240, fewer than 270, fewer than 300, fewer than 360, fewer than 420, fewer than 480, fewer than 540, or fewer than 565 amino acids. Preferably, the polypeptide fragments are fragments of SEQ ID NOS:2, 4, 8, 10, 12, or 14, and more preferably fragments of SEQ ID NOS:2, 6, 10, 12, or 14, and even more preferably fragments of SEQ ID NOS:2, 10, or 14.

The determination of a fragment eliciting an immune response in a mammal substantially similar to that of the non-fragment for at least one influenza subtype can be readily determined by one of ordinary skill. The fragment can be analyzed to contain at least one, preferably more, antigenic epitopes as provided by a publicly available database, such as the Los Alamos National Laboratory's Influenza Sequence Database. In addition, immune response studies can be routinely assessed using mice and HI titers and ELISpots analysis, such as that shown in the Examples below.

According to some embodiments of the invention, methods of inducing or eliciting an immune response in mammals against a plurality of influenza viruses comprise administering to the mammals: a) the influenza strain H5N1 consensus HA protein, functional fragments thereof, or expressible coding sequences thereof; and b) one or more isolated encoding nucleic acid molecules provided herein, protein encoded by such nucleic acid molecules, or fragments thereof.

According to some embodiments of the invention, methods of inducing or eliciting an immune response in mammals against a plurality of influenza viruses comprise administering to the mammals: a) the influenza strain H1N1 and influenza strain H5N1 consensus NA protein, functional fragments thereof, or expressible coding sequences thereof and b) one or more isolated encoding nucleic acid molecules provided herein, protein encoded by such nucleic acid molecules, or fragments thereof.

According to some embodiments of the invention, methods of inducing or eliciting an immune response in mammals against a plurality of influenza viruses comprise administering to the mammals: a) the influenza strain H1N1 and influenza strain H5N1 consensus M1 protein, functional fragments thereof, or expressible coding sequences thereof and b) one or more isolated encoding nucleic acid molecules provided herein, protein encoded by such nucleic acid molecules, or fragments thereof.

According to some embodiments of the invention, methods of inducing or eliciting an immune response in mammals against a plurality of influenza viruses comprise administering to the mammals: a) the influenza strain H5N1 M2E-NP consensus protein, functional fragments thereof, or expressible coding sequences thereof and b) one or more isolated encoding nucleic acid molecules provided herein, protein encoded by such nucleic acid molecules, or fragments thereof.

According to some embodiments of the invention, methods of inducing or eliciting an immune response in mammals against a plurality of influenza viruses comprise administering to the mammals: a) the influenza strain H1N1 HA consensus protein, functional fragments thereof, or expressible coding sequences thereof and b) one or more isolated encoding nucleic acid molecules provided herein, protein encoded by such nucleic acid molecules, or fragments thereof.

According to some embodiments of the invention, methods of inducing or eliciting an immune response in mammals against a plurality of influenza viruses comprise administering to the mammals: a) the influenza strain H3N1 HA consensus protein, functional fragments thereof, or expressible coding sequences thereof; and b) one or more isolated encoding nucleic acid molecules provided herein, protein encoded by such nucleic acid molecules, or fragments thereof.

In some embodiments of the invention, the vaccines of the invention include at least two of the following sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14, or any combination of two or more sequences from the aforementioned list.

Vaccines

In some embodiments, the invention provides improved vaccines by providing proteins and genetic constructs that encode proteins with epitopes that make them particularly effective as immunogens against which immune responses can be induced. Accordingly, vaccines can be provided to induce a therapeutic or prophylactic immune response.

According to some embodiments of the invention, a vaccine according to the invention is delivered to an individual to modulate the activity of the individual's immune system and thereby enhance the immune response. When a nucleic acid molecule that encodes the protein is taken up by cells of the individual the nucleotide sequence is expressed in the cells and the protein are thereby delivered to the individual. Aspects of the invention provide methods of delivering the coding sequences of the protein on nucleic acid molecule such as plasmid.

According to some aspects of the present invention, compositions and methods are provided which prophylactically and/or therapeutically immunize an individual.

When taken up by a cell, the DNA plasmids can stay present in the cell as separate genetic material. Alternatively, RNA may be administered to the cell. It is also contemplated to provide the genetic construct as a linear minichromosome including a centromere, telomeres and an origin of replication. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the mammals to whom the nucleic acid construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from simian virus 40 (SV40), mouse mammary tumor virus (MMTV) promoter, human immunodeficiency virus (HIV) such as the bovine immunodeficiency virus (BIV) long terminal repeat (LTR) promoter, Moloney virus, avian leukosis virus (ALV), cytomegalovirus (CMV) such as the CMV immediate early promoter, Epstein Barr virus (EBV), Rous sarcoma virus (RSV) as well as promoters from human genes such as human actin, human myosin, human hemoglobin, human muscle creatine and human metalothionein; in other embodiments, promoters can be tissue specific promoters, such as muscle or skin specific promoters, natural or synthetic. Examples of such promoters are described in US patent application publication no. US20040175727, which is incorporated hereby in its entirety.

Examples of polyadenylation signals useful to practice the present invention, especially in the production of a genetic vaccine for humans, include but are not limited to SV40 polyadenylation signals, LTR polyadenylation signals, bovine growth hormone (bGH) polyadenylation signals, human growth hormone (hGH) polyadenylation signals, and human β-globin polyadenylation signals. In particular, the SV40 polyadenylation signal that is in pCEP4 plasmid (Invitrogen, San Diego, Calif.), referred to as the SV40 polyadenylation signal, can be used.

In addition to the regulatory elements required for DNA expression, other elements may also be included in the DNA molecule. Such additional elements include enhancers. The enhancer may be selected from the group including but not limited to: human actin, human myosin, human hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration.

In order to maximize protein production, regulatory sequences may be selected which are well suited for gene expression in the cells the construct is administered into. Moreover, codons that encode said protein may be selected which are most efficiently transcribed in the host cell. One having ordinary skill in the art can produce DNA constructs that are functional in the cells.

In some embodiments, nucleic acid constructs may be provided in which the coding sequences for the proteins described herein are linked to IgE signal peptide. In some embodiments, proteins described herein are linked to IgE signal peptide.

In some embodiments for which protein is used, for example, one having ordinary skill in the art can, using well known techniques, can produce and isolate proteins of the invention using well known techniques. In some embodiments for which protein is used, for example, one having ordinary skill in the art can, using well known techniques, inserts DNA molecules that encode a protein of the invention into a commercially available expression vector for use in well known expression systems. For example, the commercially available plasmid pSE420 (Invitrogen, San Diego, Calif.) may be used for production of protein in *Escherichia coli* (*E. coli*). The commercially available plasmid pYES2 (Invitrogen, San Diego, Calif.) may, for example, be used for production in *Saccharomyces cerevisiae* strains of yeast. The commercially available MAXBAC™ complete baculovirus expression system (Invitrogen, San Diego, Calif.) may, for example, be used for production in insect cells. The commercially available plasmid pcDNA I or pcDNA3 (Invitrogen, San Diego, Calif.) may, for example, be used for production in mammalian cells such as Chinese hamster ovary (CHO) cells. One having ordinary skill in the art can use these commercial expression vectors and systems or others to produce protein by routine techniques and readily available starting materials. (See e.g., Sambrook et al., Molecular Cloning a Laboratory Manual, Second Ed. Cold Spring Harbor Press (1989)). Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers are readily available and known in the art for a variety of hosts. See e.g., Sambrook et al., Molecular Cloning a Laboratory Manual, Second Ed. Cold Spring Harbor Press (1989). Genetic constructs include the protein coding sequence operably linked to a promoter that is functional in the cell line, or cells of targeted tissue, into which the constructs are transfected. Examples of constitutive promoters include promoters from cytomegalovirus (CMV) or SV40. Examples of inducible promoters include mouse mammary leukemia virus or metallothionein promoters. Those having ordinary skill in the art can readily produce genetic constructs useful for transfecting cells with DNA that encodes protein of the invention from readily available starting materials. The expression vector including the DNA that encodes the protein is used to transform the compatible host which is then cultured and maintained under conditions wherein expression of the foreign DNA takes place.

The protein produced is recovered from the culture, either by lysing the cells or from the culture medium as appropriate and known to those in the art. One having ordinary skill in the art can, using well known techniques, isolate protein that is produced using such expression systems. The methods of purifying protein from natural sources using antibodies which specifically bind to a specific protein as described above may be equally applied to purifying protein produced by recombinant DNA methodology.

In addition to producing proteins by recombinant techniques, automated peptide synthesizers may also be employed to produce isolated, essentially pure protein. Such techniques are well known to those having ordinary skill in the art and are useful if derivatives which have substitutions not provided for in DNA-encoded protein production.

The nucleic acid molecules may be delivered using any of several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. Preferably, the nucleic acid molecules such as the DNA plasmids described herein are delivered via DNA injection and along with in vivo electroporation.

Routes of administration include, but are not limited to, intramuscular, intransally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, traditional syringes, needleless injection devices, "microprojectile bombardment gone guns", or other physical methods such as electroporation ("EP"), "hydrodynamic method", or ultrasound.

Examples of electroporation devices and electroporation methods preferred for facilitating delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Also preferred, are electroporation devices and electroporation methods for facilitating delivery of the DNA vaccines provided in co-pending and co-owned U.S. patent application Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety. Preferable, the electroporation device is the CELLECTRA™ device (VGX Pharmaceuticals, Blue Bell, Pa.), including the intramuscular (IM) and intradermal (ID) models.

U.S. Pat. No. 7,245,963 by Draghia-Akli, et al. describes modular electrode systems and their use for facilitating the introduction of a biomolecule into cells of a selected tissue in a body or plant. The modular electrode systems comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 are adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

The following is an example of methods of the present invention, and is discussed in more detail in the patent references discussed above: electroporation devices can be configured to deliver to a desired tissue of a mammal a pulse of energy producing a constant current similar to a preset current input by a user. The electroporation device comprises an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation component can function as one element of the electroporation devices, and the other elements are separate elements (or components) in communication with the electroporation component. In some embodiments, the electroporation component can function as more than one element of the electroporation devices, which can be in communication with still other elements of the electroporation devices separate from the electroporation component. The present invention is not limited by the elements of the electroporation devices existing as parts of one electromechanical or mechanical device, as the elements can function as one device or as separate elements in communication with one another. The electroporation component is capable of delivering the pulse of energy that produces the constant current in the desired tissue, and includes a feedback mechanism. The electrode assembly includes an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

In some embodiments, the plurality of electrodes can deliver the pulse of energy in a decentralized pattern. In some embodiments, the plurality of electrodes can deliver the pulse of energy in the decentralized pattern through the control of the electrodes under a programmed sequence, and the programmed sequence is input by a user to the electroporation component. In some embodiments, the programmed sequence comprises a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

In some embodiments, the feedback mechanism is performed by either hardware or software. Preferably, the feedback mechanism is performed by an analog closed-loop circuit. Preferably, this feedback occurs every 50 µs, 20 µs, 10 µs or 1 µs, but is preferably a real-time feedback or instantaneous (i.e., substantially instantaneous as determined by available techniques for determining response time). In some embodiments, the neutral electrode measures the impedance in the desired tissue and communicates the impedance to the feedback mechanism, and the feedback mechanism responds to the impedance and adjusts the pulse of energy to maintain the constant current at a value similar to the preset current. In some embodiments, the feedback mechanism maintains the constant current continuously and instantaneously during the delivery of the pulse of energy.

A pharmaceutically acceptable excipient can include such functional molecules as vehicles, adjuvants, carriers or diluents, which are known and readily available to the public. Preferably, the pharmaceutically acceptable excipient is an adjuvant or transfection facilitating agent. In some embodiments, the nucleic acid molecule, or DNA plasmid, is delivered to the cells in conjunction with administration of a polynucleotide function enhancer or a genetic vaccine facilitator agent (or transfection facilitating agent). Polynucleotide function enhancers are described in U.S. Pat. Nos. 5,593,972, 5,962,428 and International Application Serial Number PCT/US94/00899 filed Jan. 26, 1994, which are each incorporated herein by reference. Genetic vaccine facilitator agents are described in U.S. Ser. No. 021,579 filed Apr. 1, 1994, which is incorporated herein by reference. The transfection facilitating agent can be administered in conjunction with nucleic acid molecules as a mixture with the nucleic acid molecule or administered separately simultaneously, before or after administration of nucleic acid molecules. Examples of transfection facilitating agents includes surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid vaccines may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

In some preferred embodiments, the DNA plasmids are delivered with an adjuvant that are genes for proteins which further enhance the immune response against such target proteins. Examples of such genes are those which encode other cytokines and lymphokines such as alpha-interferon, gamma-interferon, platelet derived growth factor (PDGF), TNFα, TNFβ, GM-CSF, epidermal growth factor (EGF), IL-1, IL-2, IL-4, IL-5, IL-6, IL-10, IL-12, IL-18, MHC, CD80, CD86 and IL-15 including IL-15 having the signal sequence deleted and optionally including the signal peptide from IgE. Other genes which may be useful include those encoding: MCP-1, MIP-1α, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The pharmaceutical compositions according to the present invention comprise DNA quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. In some embodiments, a stabilizing agent that allows the formulation to be stable at room or ambient temperature for extended periods of time, such as LGS or other polycations or polyanions is added to the formulation.

In some embodiments, methods of eliciting an immune response in mammals against a consensus influenza antigen include methods of inducing mucosal immune responses. Such methods include administering to the mammal one or more of CTACK protein, TECK protein, MEC protein and functional fragments thereof or expressible coding sequences thereof in combination with an DNA plasmid including a consensus influenza antigen, described above. The one or more of CTACK protein, TECK protein, MEC protein and functional fragments thereof may be administered prior to, simultaneously with or after administration of the DNA plasmid influenza vaccines provided herein. In some embodiments, an isolated nucleic acid molecule that encodes one or more proteins of selected from the group consisting of: CTACK, TECK, MEC and functional fragments thereof is administered to the mammal.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Preferably the DNA formulations for use with a muscle or skin EP device described herein have high DNA concentrations, preferably concentrations that include milligram to tens of milligram quantities, and preferably tens of milligram quantities, of DNA in small volumes that are optimal for delivery to the skin, preferably small injection volume, ideally 25-200 microliters (μL). In some embodiments, the DNA formulations have high DNA concentrations, such as 1 mg/mL or greater (mg DNA/volume of formulation). More preferably, the DNA formulation has a DNA concentration that provides for gram quantities of DNA in 200 μL of formula, and more preferably gram quantities of DNA in 100 μL of formula.

The DNA plasmids for use with the EP devices of the present invention can be formulated or manufactured using a combination of known devices and techniques, but preferably they are manufactured using an optimized plasmid manufacturing technique that is described in a commonly owned, co-pending U.S. provisional application U.S. Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a commonly owned patent, U.S. Pat. No. 7,238,522, which issued on Jul. 3, 2007. The high concentrations of plasmids used with the skin EP devices and delivery techniques described herein allow for administration of plasmids into the ID/SC space in a reasonably low volume and aids in enhancing expression and immunization effects. The commonly owned application and patent, U.S. Ser. No. 60/939,792 and U.S. Pat. No. 7,238,522, respectively, are hereby incorporated in their entirety.

Example 1

Plasmid Constructs

A ubiquitous cytomegalovirus (CMV) promoter drives the expression of human secreted embryonic alkaline phosphatase (SEAP) reporter transgene product in the pCMV-SEAP vector. Plasmids were obtained using a commercially available kit (Qiagen Inc., Chatsworth, Calif.). Endotoxin levels were at less than 0.01 EU/μg, as measured by Kinetic Chromagenic LAL (Endosafe, Charleston, S.C.). Consensus HA and NA constructs were generated by analyzing primary virus sequences from 16 H5 viruses that have proven fatal to humans in recent years, and over 40 human N1 viruses. These sequences were downloaded from the Los Alamos National Laboratory's Influenza Sequence Database. After generating the consensus sequences, the constructs were optimized for mammalian expression, including the addition of a Kozak sequence, codon optimization, and RNA optimization. These constructs were then subcloned into the pVAX vector (Invitrogen, Carlsbad, Calif.). Unless indicated otherwise, plasmid preparations were diluted in sterile water and formulated 1% weight/weight with poly-L-glutamate sodium salt (LGS) (MW=10.5 kDa average)(Sigma, St. Louis, Mo.), further HPLC purified at VGX Pharmaceuticals, Immune Therapeutics Division (The Woodlands, Tex.).

Example 2

Treatment of Pigs

Pigs were divided into 10 groups×4 pigs per group for a total of 40 pigs (Table 1). Pigs were acclimated for 4 days, weighed and ear-tagged. On Study Day 0, pigs were weighed, bled and anesthetized using a combination pre-anesthetic for pigs—ketamine—(20 mg/kg), xylazine—(2.2 mg/kg) and atropine (0.04 mg/kg), and then anesthetized using isoflurane (induction at 5%, maintenance at 2-3%). Pigs (n=4/group) were injected with 0.6 mL of CMV-HA (a pVAX based construct that expresses a consensus H5 antigen), CMV-NA (a pVAX based construct that expresses a consensus N1 antigen), and CMV-SEAP (a construct expressing the reporter gene secreated ambryonic alkaline phosphatase, SEAP) plasmid (the last one added to increase plasmid concentration, and viscosity of the solution for the "muscle damage" assessment)+1.0% wt/wt LGS at varying plasmid concentrations and current intensities. The plasmids were prepared according to the materials and methods provided in Example 1. After 4 s, animals were electroporated using the adaptive constant current CELLECTRA™ intramuscular (IM) system (VGX Pharmaceuticals, Blue Bell, Pa.) equipped with 5 needle electrodes and operated with the following pulse parameters: 52 millisecond pulses, 1 second between pulses, 3 pulses with varying current (0.1, 0.3 and 0.5 A).

TABLE 1

Groups for the pig vaccine experiment

| Group | Plasmid | Conc (mg/mL) | Construct (mg)/pig | Total Dose (mg/pig) | Injection Volume | A | n |
|---|---|---|---|---|---|---|---|
| 1 | HA, NA, SEAP | 10 | 2 | 6 | 600 µl | 0.5 | 4 |
| 2 | HA, NA, SEAP | 4 | 0.8 | 2.4 | 600 µl | 0.5 | 4 |
| 3 | HA, NA, SEAP | 1.5 | 0.1 | 0.3 | 600 µl | 0.5 | 4 |
| 4 | HA, NA, SEAP | 10 | 2 | 6 | 600 µl | 0.3 | 4 |
| 5 | HA, NA, SEAP | 4 | 0.8 | 2.4 | 600 µl | 0.3 | 4 |
| 6 | HA, NA, SEAP | 1.5 | 0.1 | 0.3 | 600 µl | 0.3 | 4 |
| 7 | HA, NA, SEAP | 10 | 2 | 6 | 600 µl | 0.1 | 4 |
| 8 | HA, NA, SEAP | 4 | 0.8 | 2.4 | 600 µl | 0.1 | 4 |
| 9 | HA, NA, SEAP | 1.5 | 0.1 | 0.3 | 600 µl | 0.1 | 4 |
| 10 | None | N/A | N/A | N/A | N/A | N/A | 4 |

The area surrounding each injection site was tattooed for rapid identification for biopsy at Days 14 and 35 post-injection.

Pigs were allowed to recover from anesthesia and were closely monitored for 24 hours to ensure full recovery. Any pigs that did not fully recover within 2 to 3 hours post-treatment were noted. Pigs were weighed and bled on Day 10, Day 21 and Day 35. The pigs were administered a second vaccination on Day 21. Blood was collected in 2 purple top tubes, 1.0 mL for CBC and differentials (Antech Diagnostics, Irvine, Calif.); 10 mL for IFN-γ ELISpots against HA and NA antigens, and separate falcon tubes which were allowed to clot and centrifuged to isolate serum then aliquoted into tubes on ice. On Day 35, all pigs were exsanguinated under surgical plane of anesthesia and needle punch biopsies of the injection sites were taken for histology.

Hemagglutination Inhibition (HI) Assay

Pig sera were treated with receptor destroying enzyme (RDE) by diluting one part serum with three parts enzyme and incubated overnight in 37° C. water bath. The enzyme was inactivated by 30 min incubation at 56° C. followed by addition of six parts PBS for a final dilution of 1/10. HI assays were performed in V-bottom 96-well microtiter plates, using four HA units of virus and 1% horse red blood cells as previously described (Stephenson, I., et al., *Virus Res.,* 103(1-2):91-5 (July 2004)).

The highest titers as demonstrated by the HI assay (FIG. 2) were found in sera from the group administered 2 mg of HA-expressing plasmid at a current setting of 0.5 A (120±40; P=0.11 versus 2 mg/0.3 A and P=0.02 versus 2 mg/0.1 A); the titers decreased with the intensity of the electric field for the group that received 2 mg of each plasmid; if either plasmid quantity of current were decreased thereafter, the titers were more variable, and non-different between groups.

The HI titers were highest in the group administered 2 mg of HA-expressing plasmid and electroporated at 0.5 A. Furthermore, the titers decline with descending plasmid doses in the group electroporated at 0.5 A, and with the intensity of the electric field. The lower plasmid quantities or lower current intensities appeared to increase the intra-group variability.

HA and NA IFN-γ ELISpots

ELISpot were performed as previously described using IFN-γ capture and detection antibodies (MabTech, Sweden) (Boyer J D, et al., *J Med Primatol,* 34(5-6):262-70 (October 2005)). Antigen-specific responses were determined by subtracting the number of spots in the negative control wells from the wells containing peptides. Results are shown as the mean value (spots/million splenocytes) obtained for triplicate wells.

The group administered 2 mg of each plasmid (for a total of 4 mg) at a current setting of 0.3 A attained the highest cellular immune response as measured by the IFN-γ ELISpot of 537±322 SFU per million cells. The average responses of all other groups were within background levels of the assay. The individual ELISpot responses of two animals attaining the highest cellular immune response are highlighted in FIG. 3.

CBC Results

Lymphocytes reached the highest levels at Day 21 of the study and in the groups administered the highest dose of vaccines, regardless of current setting, although the groups with the highest dose (4 mg of total plasmid, 2 mg each) and highest current setting (0.5 A) demonstrates highest lymphocyte response, 40% higher than controls (12670±1412 vs. 7607±1603 lymphocyte counts/100 blood, respectively; P<0.002).

Muscle Histopathology

The injection sites were identified and punch biopsies were taken at Days 14 and 35 post-treatment after the pigs were exsanguinated. The tissues were fixed in buffered formalin for 24 hours then washed 3× in PBS and stored in 70% alcohol. The biopsy samples were submitted to Antech Diagnostics where they were processed and sections stained with hematoxylin and eosin (H&E). All the slides were evaluated by a single board-certified pathologist who scored them 0 to 5 for pathological criteria (Table 2) in various tissue layers (Table 3). The mean score was calculated for each group at each time point.

TABLE 2

Biopsy pathology scoring parameters

| Score | Criteria |
|---|---|
| 0 | Not present, no inflammatory cells |
| 1 | Minimal, 1-20 inflammatory cells/100x high-powered field (HPF) |
| 2 | Mild, 21-40 inflammatory cells/100x HPF |
| 3 | Moderate, 41-75 inflammatory cells/100x HPF |
| 4 | Moderate to Marked/Severe, 76-100 inflammatory cells/100x HPF |
| 5 | Marked Severe, >100 inflammatory cells/100x HPF |

TABLE 3

Biopsy tissue layers and pathological parameters

| Anatomy Location | Pathology Parameter |
| --- | --- |
| Dermal | Superficial neovascularization |
| Dermal | Pylogranulomatous inflammation |
| Dermal | Overlying erosion & inflammatory crusting |
| Dermal | Focal fibrosis |
| Subcutaneous | Pylogranulomatous inflammation with intralesional collagen necrosis |
| Subcutaneous | Lymphacytic and plasmalytic inflammation |
| Skeletal muscle | Lymphacytic and plasmalytic and eosinophilic inflammation |
| Skeletal muscle | Myocyte degeneration/necrosis |
| Skeletal muscle | Fibrosis |

The histopathology was scored from the muscle biopsy (FIG. 4A) at 14 and 35 days after plasmid injection and EP based on a 0 to 5 scale criteria (Table 2). Overall pathology scores following electroporation declined in the tissue layers (Table 3) from Day 14 to Day 35. The group that received 6 mg of total plasmid at 0.3 A settings exhibited the highest total pathology scores at Day 14 (18.3±6.4, P<0.0002 versus control), correlating with the highest average lymphocyte responses. All pathology scores at Day 35 approached levels of non-treated control levels (range of 6.67 to 4.25). Nevertheless, when the muscle necrosis and fibrosis (typically associated with the EP procedure) (Gronevik E, et al., *J Gene Med*, 7(2):218-27 (2005 February)). were analyzed separately (FIG. 4B), the scores ranged between 1 and 2, with no difference between groups or between treated groups and controls, while the higher scores were associated with lymphatic, plasmacytic or eosinophilic inflammation due to immune responses. Significantly, these scores also declined from day 14 to day 35 post-treatment.

Data Analysis

Data were analyzed using Microsoft Excel Statistics package. Values shown in the figures are the mean±SEM. Specific values were obtained by comparison using one-way ANOVA and subsequent t-test. A value of p<0.05 was set as the level of statistical significance.

Example 3

Treatment of Ferrets

Twenty male ferrets (Triple F Farms, Sayre, Pa.), 4-6 months of age or at least 1 kg body weight, were used in this study and housed at BIOQUAL, Inc. (Rockville, Md.). The ferret study design is in Table 4. Animals were allowed to acclimate for two weeks prior to the study. Animals were immunized (under anesthesia) at Week 0, 4, and 9. Blood was drawn every 2 weeks. After the third immunization, animals were moved into a BSL-3 facility and challenged at Week 13 with a very potent strain of avian influenza (H5N1) and then followed for two more weeks post-challenge. For two weeks after challenge, animals were monitored daily, and body weights, temperature and clinical scores were recorded. Activity level was monitored and recorded; death were documented.

Figure 6:
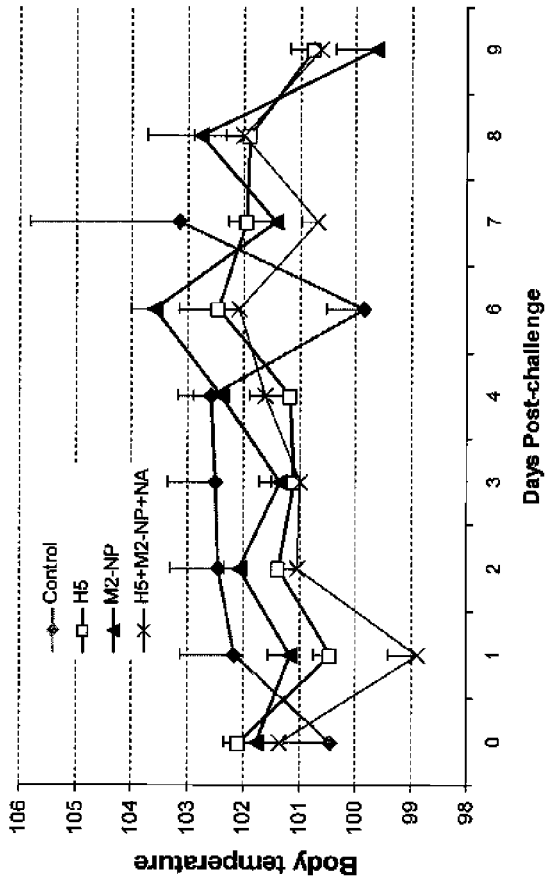
Figure 7:
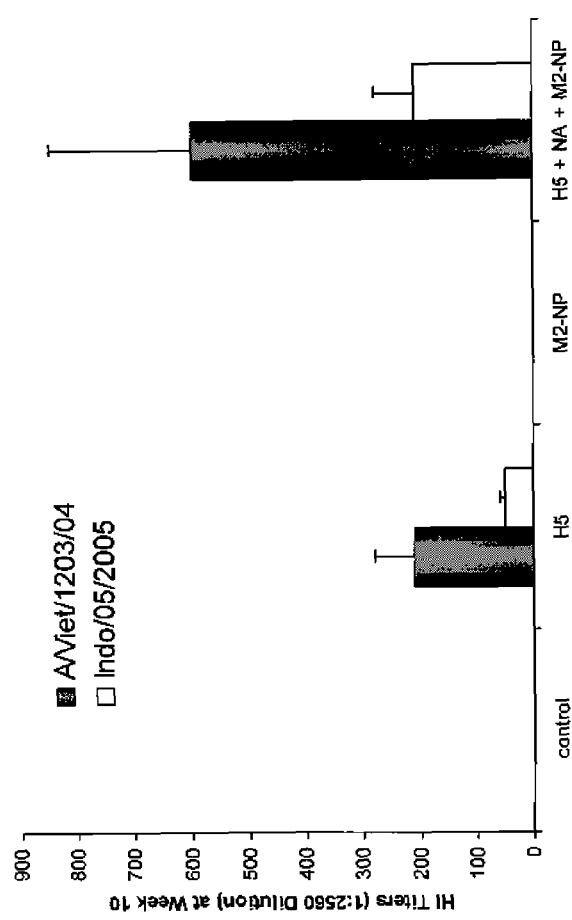

This study tested the efficacy of HA, NA and M2e-NP DNA vaccine delivered IM followed by electroporation using the CELLECTRA™ adaptive constant current electroporation intramuscular (IM) system (VGX Pharmaceuticals, Blue Bell, Pa.) in an influenza challenge model in ferrets. The DNA plasmids were prepared according to the materials and methods provided in Example 1. As outlined in Table 4, animals in Groups 2, 3 and 4 received 0.2 mg of the respective influenza plasmid vaccine. In order to correct for dose, groups which received 1 plasmid vaccine (Groups 2 and 3) or no vaccine (control Group 1), the difference was made up by pVAX empty vector such that all animals in every group received a total dose of 0.6 mg of plasmid. The conditions of electroporation were, using a 5 needle electrode array: 0.5 Amps, 52 msec pulse width, 1 sec between pulses, 4 sec delay between injection and electroporation.

TABLE 4

Groups for the Influenza challenge experiment in ferrets

| Group | Plasmids/Antigens | Vaccine Dose (mg) per Plasmid | Total vaccine in Total volume | n |
|---|---|---|---|---|
| 1 | None (pVAX only) | 0 mg | 0.6 mg in 0.6 mL | 4 |
| 2 | H5 + pVAX | 0.2 mg | 0.6 mg in 0.6 mL | 4 |
| 3 | NA + pVAX | 0.2 mg | 0.6 mg in 0.6 mL | 4 |
| 4 | H5, NA, M2e-NP | 0.2 mg | 0.6 mg in 0.6 mL | 4 |

Hemagglutination Inhibition (HI) Assay

Sera were treated with receptor destroying enzyme (RDE) by diluting one part serum with three parts enzyme and incubated overnight in 37° C. water bath. The enzyme was inactivated by 30 min incubation at 56° C. followed by addition of six parts PBS for a final dilution of 1/10. HI assays were performed in V-bottom 96-well microtiter plates, using four HA units of virus and 1% horse red blood cells as previously described (Stephenson, I., et al., *Virus Res.,* 103(1-2):91-5 (July 2004)). The viruses used for the HI assay are reassortant strains we obtained from the Center for Disease Control: A/Viet/1203/2004(H5N1)/PR8-IBCDC-RG (clade 1 virus) and A/Indo/05/2005 (H5N1)/PR8-IBCDC-RG2 (clade 2 virus). The ferret model of influenza infection is considered to be more reflective of human disease and a more rigorous challenge model. Ferrets exhibit similar symptoms to humans infected with influenza and similar tissue tropism with regards to human and avian influenza viruses. Serum collected at different time points throughout the study was used to detect HI activity against H5N1 viruses. As shown in FIG. 7, both groups containing the consensus H5 specific HA construct attained protective levels of antibody (>1:40) after two immunizations and were also able to inhibit a Glade 2 H5N1 virus. In other words, the HI assay was positive against both viral strains despite the consensus HA strain was based on Glade 1 viruses.

Data Analysis

Data were analyzed using Microsoft Excel Statistics package. Values shown in the figures are the mean±SEM. Specific values were obtained by comparison using one-way ANOVA and subsequent t-test. A value of $p<0.05$ was set as the level of statistical significance.

Ferret Influenza Challenge

The results of the influenza challenge are depicted in FIGS. 5 and 6. Control animals lost 25% of their body weight on average post-challenge (FIG. 5), while animals vaccinated with HA (Group 1) or HA+M2e-NP+NA (Group 4) lost between 9 and 10% (*$P<0.004$ versus controls). Body temperatures were elevated in control animals until all control animals were either found dead or euthanized by Day 8 (FIG. 6). All animals vaccinated, regardless of which vaccine regimen, survived the challenge and showed fewer signs of infection as compared to the control animals as evidenced by their clinical scores (Table 5). Control animals worsen as far as clinical scores (nasal discharge, cough, lethargy), and died between day 5 and day 7 post-challenge. As shown in Table 5, the severity of the clinical scores in vaccinated animals was inversely correlated with the antibody titers (higher antibody titers, lower clinical scores, better clinical outcome).

All plasmids were formulated at 10 mg/mL in water for injection+1% LGS, as described in previous examples, above, and mixed into a single solution PER STUDY GROUP (S) (Groups C, D, G, and H, in above table, Table 6). The correct injection volume for each group designated IM CELLECTRA™ EP (VGX Pharmaceuticals), ID CELLECTRA™ EP (VGX Pharmaceuticals), and IM Syringe was calculated. For the ID administration, if the required injection volume surpassed 100 µL per site, the formulation was split into a number of injection sites (2, 3, or 6 depending on how many total mg of vaccine were administered). The animals

TABLE 5

Results for Challenged Ferrets

| Vaccines | Ferret | Day 1 | Day 2 | Day 3 | Day 5 | Day 6 | Day 7 | Day 8 | Day 9 | HI Titers 3 wks Pre-challenge |
|---|---|---|---|---|---|---|---|---|---|---|
| Control (pVAX) | 891 | 0_1 | 1_1 | 1_1 | 0_1 | 0_1 | 1_1* | | | <20 |
| | 890 | 0_1 | 1_1 | 1_1 | 0_1* | | | | | <20 |
| | 877 | 0_1 | 0_1 | 1_1 | 0_2 | 2_3 | FD | | | <20 |
| | 876 | 0_1 | 0_1 | 0_1 | 0_1 | 2_3 | 1_3* | | | <20 |
| H5 | 878 | 0_1 | 0_1 | 1_1 | 0_1 | 0_1 | 0_1 | 0_1 | 0_1 | 40 |
| | 879 | 0_1 | 0_1 | 0_1 | 0_1 | 0_1 | 0_1 | 0_1 | 0_1 | 320 |
| | 888 | 0_1 | 0_1 | 0_1 | 0_1 | 0_1 | 0_1 | 0_1 | 0_1 | 160 |
| | 889 | 0_1 | 0_1 | 0_1 | 0_1 | 0_1 | 0_1 | 0_1 | 0_1 | 320 |
| M2-NP | 881 | 0_1 | 0_1 | 1_0 | 0_1 | 0_1 | 1_1 | 0_1 | 0_1 | <20 |
| | 880 | 0_1 | 0_1 | 0_0 | 0_1 | 0_1 | 0_1 | 0_1 | 0_1 | <20 |
| | 883 | 0_1 | 1_1 | 1_1 | 0_1 | 0_1 | 1_1 | 0_1 | 0_1 | <20 |
| | 882 | 0_1 | 0_1 | 1_1 | 0_1 | 0_1 | 1_2 | 0_2 | 0_1 | <20 |
| H5 + M2-NP + NA | 885 | 0_1 | 0_1 | 0_1 | 0_1 | 0_1 | 0_1 | 0_1 | 0_1 | 1280 |
| | 884 | 0_1 | 0_1 | 0_1 | 0_1 | 0_1 | 0_1 | 0_1 | 0_1 | 320 |
| | 886 | 1_1 | 1_1 | 0_1 | 0_1 | 0_1 | 1_1 | 0_1 | 1_1 | 160 |
| | 887 | 0_1 | 1_1 | 0_0 | 0_1 | 0_1 | 1_1 | 0_1 | 0_1 | 640 |

Table 5 Note:
Clinical scores are depicted for the post-challenge observation period. A "*" indicates the animal was euthanized; FD = found dead. The first clinical score in each column is for nasal symptoms: 0 = none; 1 = nasal discharge; 2 = breathing from mouth. The second score is for activity: 0 = sleeping; 1 = bright and alert; 2 = alert but non-responsive; 3 = lethargic. The HI titers for each animal measured 3 weeks pre-challenge are depicted for comparison purposes.

Example 4

Intradermal Delivery Comparisons with Intramuscular Delivery in Primates

Rhesus macaques were immunized in these studies. Animals were acclimated for 2 months prior to the start of experiments. The study progressed as follows: Week 0—performed 1st immunization (plasmid dose administration) and baseline bleed; Week 2 performed bleed; Week 3 performed 2nd immunization (plasmid dose administration); Week 5 performed bleed; Week 6 performed 3rd immunization (plasmid dose administration) and bleed; Week 8 performed bleed.

that received IM injection(s) were given the entire formulation in one single site.

The CELLECTRA™ adaptive constant current device used in the pigs experiments, ferret experiments and nonhuman experiments described in the Examples. The electroporation conditions were as following: for the IM injection and electroporation groups, the conditions were: 0.5 Amps, 52 msec/pulse, three pulses, 4 sec delay between plasmid injection and electroporation. For the ID injection and electroporation groups, the conditions were: 0.2 Amps, 52 msec/pulse, three pulses, 4 sec delay between plasmid injection and electroporation.

TABLE 6

| Study Group | DNA Constructs | Nr. | Route of Admin | Dose | Total DNA (mg) |
|---|---|---|---|---|---|
| A | DNA 6 + 9 | 5 | IM CELLECTRA ™ EP | 1 mg/Const | 2 |
| B | DNA 6 + 9 | 5 | ID CELLECTRA ™ EP | 1 mg/Const | 2 |
| C | DNA 1 + 6 + 9 + 10 | 5 | IM Syringe | 1 mg/Const | 4 |
| D | Negative Control | 5 | N/A | | 0 |

| DNA Construct # | Encoding Antigen |
|---|---|
| 1 | Non-influenza antigen control plasmid |
| 6 | Influenza H5 consensus |
| 9 | Non-influenza antigen control plasmid |
| 10 | Non-influenza antigen control plasmid |

Hemagglutination Inhibition (HI) Assay—monkey sera were treated with receptor destroying enzyme (RDE) by diluting one part serum with three parts enzyme and incubated overnight in 37° C. water bath. The enzyme was inactivated by 30 min incubation at 56° C. followed by addition of six parts PBS for a final dilution of 1/10. HI assays were performed in V-bottom 96-well microtiter plates, using four HA units of virus and 1% horse red blood cells. The data presented herein are the results after the second immunization (bleed collected before the third immunization).

Figure 8:
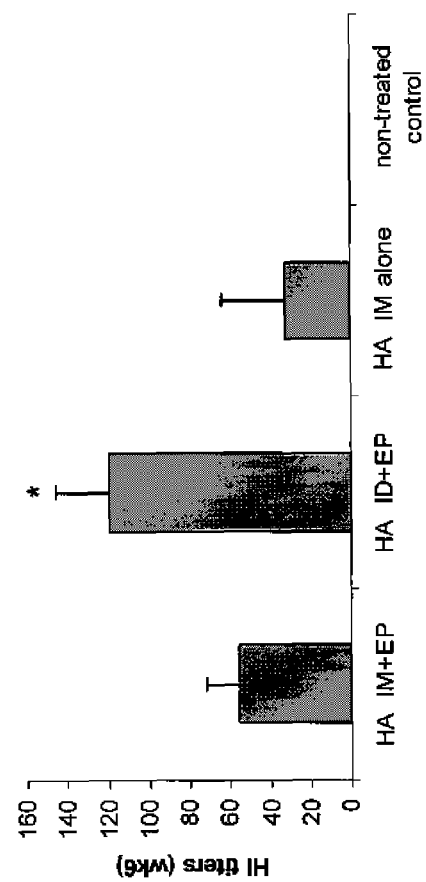

HI titers were measured three weeks after the second immunization. The results can be seen displayed in the graph in FIG. 8. Monkeys receiving the HA plasmid vaccine via ID injection followed by electroporation demonstrated more than twice the average titers of the IM+EP group and almost three times the average titers of the IM group alone (*P<0.03). Non-treated controls did not exhibit any HI titers.

Example 5

Cross Protection in Primates

Using Delivery Method—ID Injection Followed by Electroporation (EP)

Studies in non-human primates with the influenza vaccine (including H5, NA and M2e-NP consensus antigens, see above) indicated that ID injection followed by electroporation elicited higher antibody responses to the vaccine antigens than in IM injections. In one of our non-human primate studies (NHP) animals were vaccinated per Table 7.

TABLE 7

Study design and conditions. Rhesus macaques were immunized at weeks 0, 4, and 8.

| Group | n/group | Antigen | Delivery | Concentration (mg/plasmid) | EP Conditions |
|---|---|---|---|---|---|
| 1 | 5 | pVax (sham) | IM | 1 mg/construct | 0.5 Amps, 3 pulses, 52 msec, 1 sec between pulses |
| 2 | 5 | H5, NA, M2e-NP | IM | 1 mg/construct | 0.5 Amps, 3 pulses, 52 msec, 1 sec between pulses |
| 3 | 5 | M2e-NP | IM | 1 mg/construct | 0.5 Amps, 3 pulses, 52 msec, 1 sec between pulses |
| 4 | 5 | H5, NA, M2e-NP | ID | 1 mg/construct | 0.2 Amps, 2X2 pulses, 52 msec, 1 sec between pulses |

Each animal received three vaccinations, and HAI titers and microneutralization were performed for both the same Glade and cross-clades. As shown, the consensus vaccine offered broad protection not only within the same clade, but also cross-clades. Results are included in Table 8.

TABLE 8

Results of hemagglutination (HAI) and microneutralization assays.

| | Clade 1 A/Vietnam | Clade 2.1 A/Indonesia | Clade 2.2 A/Turkey | Clade 2.3.4 A/Anhui |
|---|---|---|---|---|
| HAI Assay 2nd immunization | | | | |
| VGX-3400 IM | 160 (80-320) | 36 (20-80) | 110 (0-320)$^{4/5}$ | 80 (40-160) |
| VGX-3400 ID | 664 (40-1280) | 120 (20-320) | 205 (0-320)$^{4/5}$ | 592 (40-1280) |
| 3rd immunization | | | | |
| VGX-3400 IM | 288 (160-640) | 32 (0-80)$^{3/5}$ | 36 (20-80) | 84 (20-160) |
| VGX-3400 ID | 416 (160-640) | 64 (0-160)$^{2/5}$ | 145 (20-320) | 276 (20-640) |
| Microneutralization 3rd immunization | | | | |
| VGX-3400 IM | 144 (40-360) | 8 (0-40)$^{1/5}$ | 32 (0-80)$^{2/5}$ | 88 (0-160)$^{4/5}$ |
| VGX-3400 ID | 740 (20-2560) | 96 (0-320)$^{3/5}$ | 296 (0-1280)$^{3/5}$ | 1172 (20-2560) |

Values presented indicate the mean titer, the range (in parenthesis) and the number of responders if less than 5/5 (in superscript).

Note:

HAI titers >1:20 are generally considered seroprotective in the NHP model.

The needles in the ID electroporation device are much shorter (~5 mm), of a lower gauge, and do not elicit muscle contractions or visible pain responses in the animals tested to date. Furthermore, the required electric field for efficacious ID EP is lower than that required for an optimum IM delivery. ID injection has been shown to elicit better immune responses to influenza vaccine antigens. (Holland D, et. al. (2008). *J Inf Dis.* 198:650-58.) Usually, a lower dose is needed in vaccines delivered ID compared to IM delivery to achieve similar humoral responses.

What is claimed is:

1. A DNA plasmid vaccine capable of generating in a mammal an immune response against a plurality of influenza virus subtypes, comprising:
a DNA plasmid capable of expressing a consensus influenza antigen in a cell of the mammal in a quantity effective to elicit an immune response in the mammal, the consensus influenza antigen comprising consensus hemagglutinin (HA) subtype H1 and
a pharmaceutically acceptable excipient;
the DNA plasmid comprising a promoter operably linked to a coding sequence that encodes the consensus influenza antigen HA subtype H1, and the DNA plasmid vaccine having a concentration of total DNA plasmid of 1 mg/ml or greater, wherein the coding sequence that encodes the consensus HA subtype H1 comprises SEQ ID NO:9.

2. The DNA plasmid vaccine of claim 1, wherein the coding sequence that encodes the consensus HA subtype H1 further comprises a coding sequence that encodes an IgG leader sequence attached at the 5' end of the coding sequence that encodes the consensus HA subtype H1 and is operably linked to the promoter.

3. The DNA plasmid vaccine of claim 1, wherein coding sequence that encodes the consensus HA subtype H1 further comprises a coding sequence that encodes a polyadenylation sequence attached at the 3' end of the coding sequence that encodes the consensus HA subtype H1.

4. The DNA plasmid vaccine of claim 1 wherein the pharmaceutically acceptable excipient is an adjuvant.

5. The DNA plasmid vaccine of claim 4, wherein the adjuvant is selected from the group consisting of: IL-12 and IL-15.

6. The DNA plasmid vaccine of claim 1, wherein the pharmaceutically acceptable excipient is a transfection facilitating agent.

7. The DNA plasmid vaccine of claim 6, wherein the transfection facilitating agent is a polyanion, polycation, or lipid.

8. The DNA plasmid vaccine of claim 6, wherein the transfection facilitating agent is poly-L-glutamate.

9. The DNA plasmid vaccine of claim 6, wherein the transfection facilitating agent is poly-L-glutamate at a concentration less than 6 mg/ml.

10. The DNA plasmid vaccine of claim 1, wherein said DNA plasmid vaccines comprises a plurality of different DNA plasmids; said DNA plasmid vaccine further comprising one of the plurality of DNA plasmids comprises a sequence that encodes a consensus NA, and one of the plurality of DNA plasmids comprises a sequence that encodes a consensus M2e-NP.

11. The DNA plasmid vaccine of claim 10, wherein the consensus NA is SEQ ID NO:4.

12. The DNA plasmid vaccine of claim 10, wherein the sequence that encodes consensus NA is SEQ ID NO:3.

13. The DNA plasmid vaccine of claim 10, wherein the consensus M2e-NP is SEQ ID NO:8.

14. The DNA plasmid vaccine of claim 10, wherein the sequence that encodes consensus M2e-NP is SEQ ID NO:7.

15. The DNA plasmid vaccine of claim 1, further comprising:

a DNA plasmid comprising a sequence that encodes a consensus H3, a DNA plasmid comprising a sequence that encodes a consensus H5, a DNA plasmid comprising a sequence that encodes a consensus NA, and a DNA plasmid comprising a sequence that encodes a consensus M2e-NP.

16. The DNA plasmid vaccine of claim 15, wherein the consensus H3 is SEQ ID NO:12.

17. The DNA plasmid vaccine of claim 15, wherein the sequence encoding consensus H3 is SEQ ID NO:11.

18. The DNA plasmid vaccine of claim 15, wherein the consensus NA is SEQ ID NO:4.

19. The DNA plasmid vaccine of claim 15, wherein the sequence encoding consensus NA is SEQ ID NO:3.

20. The DNA plasmid vaccine of claim 15, wherein consensus M2e-NP is SEQ ID NO:8.

21. The DNA plasmid vaccine of claim 15, wherein the sequence encoding consensus M2e-NP is SEQ ID NO:7.

22. The DNA plasmid vaccine of claim 10, wherein the mammal is a primate.

23. The DNA plasmid vaccine of claim 15, wherein the mammal is a primate.

24. The DNA plasmid vaccine of claim 1, wherein the immune response is a humoral response.

25. The DNA plasmid vaccine of claim 1, wherein the immune response is a cellular response.

26. The DNA plasmid vaccine of claim 1, wherein the immune response is a combined humoral response and cellular response.

27. A method of eliciting an immune response against a plurality of influenza virus subtypes in a mammal, comprising,
  delivering a DNA plasmid vaccine of claim 1 to tissue of the mammal, and
  electroporating cells of the tissue with a pulse of energy at a constant current effective to permit entry of the DNA plasmids in the cells.

28. The method of claim 27, wherein the delivering step comprises: injecting the DNA plasmid vaccine into intradermic, subcutaneous or muscle tissue.

29. The method of claim 27, comprising:
  presetting a current that is desired to be delivered to the tissue; and
  electroporating cells of the tissue with a pulse of energy at a constant current that equals the preset current.

30. The method of claim 29, wherein the electroporating step further comprises: measuring the impedance in the electroporated cells; adjusting energy level of the pulse of energy relative to the measured impedance to maintain a constant current in the electroporated cells; wherein the measuring and adjusting steps occur within a lifetime of the pulse of energy.

31. The method of claim 29, wherein the electroporating step comprises: delivering the pulse of energy to a plurality of electrodes according to a pulse sequence pattern that delivers the pulse of energy in a decentralized pattern.

32. A DNA plasmid comprising a coding sequence operably linked to a promoter which functions in a cell of a mammal, wherein the coding sequence encodes consensus influenza antigen hemagglutinin (HA) subtype H1 and comprises SEQ ID NO:9.

33. The DNA plasmid of claim 32, wherein coding sequence that encodes the consensus HA subtype H1 further comprises a coding sequence that encodes an IgG leader sequence attached at the 5' end of the coding sequence that encodes the consensus HA subtype H1 and operably linked to the promoter.

34. The DNA plasmid of claim 32, wherein coding sequence that encodes the consensus HA subtype H1 further comprises a coding sequence that encodes a polyadenylation sequence attached at the 3' end of the coding sequence that encodes the consensus HA subtype H1.

35. The DNA plasmid of claim 32, wherein the encoding sequence that encodes consensus HA is SEQ ID NO:9.

36. The DNA plasmid of claim 32, wherein the consensus NA is SEQ ID NO:4.

37. The DNA plasmid of claim 32, wherein the encoding sequence that encodes consensus NA is SEQ ID NO:3.

38. The DNA plasmid of claim 32, wherein the consensus M2e-NP is SEQ ID NO:8.

39. The DNA plasmid of claim 32, wherein the encoding sequence that encodes consensus M2e-NP is SEQ ID NO:7.

40. The DNA plasmid of claim 32, wherein the DNA plasmid comprises SEQ ID NO: 15, SEQ ID NO:16 or SEQ ID NO:17.

41. A DNA molecule comprising a nucleotide sequence comprising SEQ ID NO:9 or a fragment thereof that is an at least 1380 or more nucleotide fragment of SEQ ID NO:9.

42. The DNA molecule of claim 41 comprising a nucleotide sequence that is a fragment of SEQ ID NO:9 that is at least 1440 or more nucleotide fragment of SEQ ID NO:9.

43. The DNA molecule of claim 41 comprising a nucleotide sequence that is a fragment of SEQ ID NO:9 that is at least 1500 or more nucleotide fragment of SEQ ID NO:9.

44. The DNA molecule of claim 41 comprising a nucleotide sequence that is a fragment of SEQ ID NO:9 that is at least 1560 or more nucleotide fragment of SEQ ID NO:9.

45. The DNA molecule of claim 41 comprising a nucleotide sequence that is a fragment of SEQ ID NO:9 that is at least 1620 or more nucleotide fragment of SEQ ID NO:9.

46. The DNA molecule of claim 41 comprising a nucleotide sequence that is a fragment of SEQ ID NO:9 that is at least 1680 or more nucleotide fragment of SEQ ID NO:9.

47. The DNA molecule of claim 41 comprising a nucleotide sequence that is a fragment of SEQ ID NO:9 that is at least 1740 or more nucleotide fragment of SEQ ID NO:9.

48. The DNA molecule of claim 41 comprising SEQ ID NO:9.

49. The DNA molecule of claim 41 comprising SEQ ID NO:9 operably linked to a promoter which functions in a cell of a mammal.

50. The DNA molecule of claim 41 comprising SEQ ID NO:9 and further comprising a coding sequence that encodes an IgE leader sequence.

51. The DNA molecule of claim 41 comprising SEQ ID NO:9 and further comprising a polyadenylation signal linked thereto.

52. The DNA molecule of claim 41 further comprising one or more coding sequences that encode influenza antigens selected from the group consisting of: a sequence that encodes an influenza H3 antigen, a sequence that encodes an influenza H5 antigen, a sequence that encodes an influenza NA antigen, and a sequence that encodes an influenza M2e-NP antigen.

* * * * *

UNITED STATES PATENT AND TRADEMARK OFFICE
CERTIFICATE OF CORRECTION

PATENT NO. : 8,133,723 B2
APPLICATION NO. : 13/158150
DATED : March 13, 2012
INVENTOR(S) : Draghia-Akli et al.

Page 1 of 1

It is certified that error appears in the above-identified patent and that said Letters Patent is hereby corrected as shown below:

The Title page under item (73) Assignee please add: VGX Pharmaceuticals, Inc., Blue Bell, PA (US)

Signed and Sealed this
Fifteenth Day of May, 2012

David J. Kappos
*Director of the United States Patent and Trademark Office*

SEQUENCE LISTING

<160> NUMBER OF SEQ ID NOS: 17

<210> SEQ ID NO 1
<211> LENGTH: 1707
<212> TYPE: DNA
<213> ORGANISM: Artificial Sequence
<220> FEATURE:
<223> OTHER INFORMATION: Influenza H5N1 HA consensus sequence

<400> SEQUENCE: 1

```
atggaaaaga tcgtgctgct gttcgccatc gtgagcctgg tgaagagcga ccagatctgc      60
atcggctacc acgccaacaa cagcaccgag caggtggaca ccatcatgga aaaaaacgtg     120
accgtgaccc acgcccagga catcctggaa aagacccaca acggcaagct gtgcgacctg     180
gacggcgtga agcccctgat cctgcgggac tgcagcgtgg ccggctggct gctgggcaac     240
cccatgtgcg acgagttcat caacgtgccc gagtggagct acatcgtgga aaggccaac      300
ccgtgaacg acctgtgcta ccccggcgac ttcaacgact acgaggaact gaagcacctg     360
ctgtcccgga tcaaccactt cgagaagatc cagatcatcc caagagcag ctggtccagc      420
cacgaggcca gcctgggcgt gagcagcgcc tgcccatacc agggcaagtc cagcttcttc     480
cggaacgtgg tgtggctgat caagaagaac agcacctacc caccatcaa gcggagctac      540
aacaacacca ccaggaaga tctgctggtc ctgtgggca tccaccaccc caacgacgcc       600
gccgagcaga ccaagctgta ccagaacccc accacctaca tcagcgtggg caccagcacc     660
ctgaaccagc ggctggtgcc ccggatcgcc acccggtcca aggtgaacgg ccagagcggc     720
cggatggaat tcttctggac catcctgaag cccaacgatg ccatcaactt cgagagcaac     780
ggcaacttca tcgcccccga gtacgcctac aagatcgtga agaagggcga cagcaccatc     840
atgaagagcg agctggaata cggcaactgc aacaccaagt gccagacccc catgggcgcc     900
atcaacagca gcatgccctt ccacaacatc cacccctga ccatcggcga gtgccccaag      960
tacgtgaaga gcaacaggct ggtgctggcc accggcctgc ggaacagccc ccagcgggag    1020
cggcgggcc ccgcccgggg cctgttcggc gccatcgccg gcttcatcga gggcggctgg     1080
cagggcatgg tggacgggtg gtacggctac caccacagca atgagcaggg cagcggctac    1140
gccgccgaca agagagcac ccagaaggcc atcgacggc tcaccaacaa ggtgaacagc      1200
atcatcgaca agatgaacac ccagttcgag gccgtgggcc gggagttcaa caacctggaa    1260
cggcggatcg agaacctgaa caagaaaatg gaagatggct cctggacgt gtggacctac     1320
aacgccgagc tgctggtgct gatggaaaac gagcggaccc tggacttcca cgacagcaac    1380
gtgaagaacc tgtacgacaa agtgcggctg cagctgcggg acaacgccaa agagctgggc    1440
aacggctgct tcgagttcta ccacaagtgc gacaacgagt gcatggaaag cgtgcggaac    1500
ggcacctacg actaccccca gtacagcgag aagcccggc tgaagcggga ggaaatcagc     1560
ggcgtgaaac tggaaagcat cggcatctac cagatcctga gcatctacag caccgtggcc    1620
agcagcctgg ccctggccat catggtggcc ggcctgagcc tgtggatgtg cagcaacggc    1680
agcctgcagt gccggatctg catctag                                        1707
```

<210> SEQ ID NO 2
<211> LENGTH: 568
<212> TYPE: PRT
<213> ORGANISM: Artificial Sequence
<220> FEATURE:
<223> OTHER INFORMATION: Influenza H5N1 HA consensus sequence

<400> SEQUENCE: 2

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Ala Ala Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380
```

```
Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
            405                 410                 415

Asn Asn Leu Glu Arg Arg Ile Glu Leu Asn Lys Lys Met Glu Asp
        420                 425                 430

Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Ile Tyr Gln Ile Leu Ser Ile Tyr Ser Thr Val Ala Ser Ser Leu Ala
530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 3
<211> LENGTH: 1466
<212> TYPE: DNA
<213> ORGANISM: Artificial Sequence
<220> FEATURE:
<223> OTHER INFORMATION: Influenza H1N1&H5N1 NA consensus sequence

<400> SEQUENCE: 3
ggtaccgaat cgccaccat  ggactggacc tggatcctgt tcctggtggc cgctgccacc    60
cgggtgcaca gcatgaaccc caaccagaag atcatcacca tcggcagcat ctgcatggtg   120
atcggcatcg tgagcctgat gctgcagatc ggcaacatga tcagcatctg ggtgtcccac   180
agcatccaga ccggcaacca gcaccaggcc gagcccatca gcaacaccaa ctttctgacc   240
gagaaggccg tggccagcgt gaccctggcc ggcaacagca gcctgtgccc catcagcggc   300
tgggccgtgt acagcaagga caacagcatc cggatcggca gcaagggcga cgtgttcgtg   360
atccgggagc ccttcatcag ctgcagccac ctggaatgcc ggaccttctt cctgacccag   420
ggggccctgc tgaacgacaa gcacagcaac ggcaccgtga aggacagaag ccccctaccgg   480 accctgatga gctgccccgt gggcgaggcc cccagcccct acaacagccg gttcgagagc   540
gtggcctggt ccgccagcgc ctgccacgac ggcaccagct ggctgaccat cggcatcagc   600
ggccctgaca acggcgccgt ggccgtgctg aagtacaacg gcatcatcac cgacaccatc   660
aagagctggc ggaacaacat cctgcggacc caggaaagcg agtgcgcctg cgtgaacggc   720
agctgcttca ccgtgatgac cgacggcccc agcaacggcc aggccagcta caagatcttc   780
aagatggaaa agggcaaggt ggtgaagagc gtggagctgg acgcccccaa ctaccactac   840
gaggaatgca gctgctaccc cgacgccggc gagatcacct gcgtgtgccg ggacaactgg   900
cacggcagca accggccctg ggtgtccttc aaccagaacc tggaatacca gatcggctac   960
atctgcagcg gcgtgttcgg cgacaacccc aggcccaacg atggcaccgg cagctgcggc  1020
```

-continued

```
cctgtgagcg ccaacggcgc ctacggcgtg aagggcttca gcttcaagta cggcaacggc    1080
gtgtggatcg ccggaccaa gagcaccaac agcagatccg gcttcgagat gatctgggac     1140
cccaacggct ggaccgagac cgacagcagc ttcagcgtga agcaggacat cgtggccatc    1200
accgactggt ccggctacag cggcagcttc gtgcagcacc ccgagctgac cggcctggac    1260
tgcatccggc cctgcttttg gtggagctg atcagaggca ggcccaaaga gagcaccatc     1320
tggaccagcg gcagcagcat cagcttttgc ggcgtgaaca gcgacaccgt gagctggtcc    1380
tggcccgacg gcgccgagct gcccttcacc atcgacaagt accccctacga cgtgcccgac   1440 tacgcctgat gagcggccgc gagctc                                          1466
```

<210> SEQ ID NO 4
<211> LENGTH: 476
<212> TYPE: PRT
<213> ORGANISM: Artificial Sequence
<220> FEATURE:
<223> OTHER INFORMATION: Influenza H1N1&H5N1 NA consensus sequence

<400> SEQUENCE: 4

```
Met Asp Trp Thr Trp Ile Leu Phe Leu Val Ala Ala Thr Arg Val
1               5                   10                  15

His Ser Met Asn Pro Asn Gln Lys Ile Ile Thr Ile Gly Ser Ile Cys
            20                  25                  30

Met Val Ile Gly Ile Val Ser Leu Met Leu Gln Ile Gly Asn Met Ile
        35                  40                  45

Ser Ile Trp Val Ser His Ser Ile Gln Thr Gly Asn Gln His Gln Ala
    50                  55                  60

Glu Pro Ile Ser Asn Thr Asn Phe Leu Thr Glu Lys Ala Val Ala Ser
65                  70                  75                  80

Val Thr Leu Ala Gly Asn Ser Ser Leu Cys Pro Ile Ser Gly Trp Ala
                85                  90                  95

Val Tyr Ser Lys Asp Asn Ser Ile Arg Ile Gly Ser Lys Gly Asp Val
            100                 105                 110

Phe Val Ile Arg Glu Pro Phe Ile Ser Cys Ser His Leu Glu Cys Arg
        115                 120                 125

Thr Phe Phe Leu Thr Gln Gly Ala Leu Leu Asn Asp Lys His Ser Asn
    130                 135                 140

Gly Thr Val Lys Asp Arg Ser Pro Tyr Arg Thr Leu Met Ser Cys Pro
145                 150                 155                 160

Val Gly Glu Ala Pro Ser Pro Tyr Asn Ser Arg Phe Glu Ser Val Ala
                165                 170                 175

Trp Ser Ala Ser Ala Cys His Asp Gly Thr Ser Trp Leu Thr Ile Gly
            180                 185                 190

Ile Ser Gly Pro Asp Asn Gly Ala Val Ala Val Leu Lys Tyr Asn Gly
        195                 200                 205

Ile Ile Thr Asp Thr Ile Lys Ser Trp Arg Asn Asn Ile Leu Arg Thr
    210                 215                 220

Gln Glu Ser Glu Cys Ala Cys Val Asn Gly Ser Cys Phe Thr Val Met
225                 230                 235                 240

Thr Asp Gly Pro Ser Asn Gly Gln Ala Ser Tyr Lys Ile Phe Lys Met
                245                 250                 255

Glu Lys Gly Lys Val Val Lys Ser Val Glu Leu Asp Ala Pro Asn Tyr
            260                 265                 270

His Tyr Glu Glu Cys Ser Cys Tyr Pro Asp Ala Gly Glu Ile Thr Cys
        275                 280                 285
```

```
Val Cys Arg Asp Asn Trp His Gly Ser Asn Arg Pro Trp Val Ser Phe
    290                 295                 300
Asn Gln Asn Leu Glu Tyr Gln Ile Gly Tyr Ile Cys Ser Gly Val Phe
305                 310                 315                 320
Gly Asp Asn Pro Arg Pro Asn Asp Gly Thr Gly Ser Cys Gly Pro Val
                325                 330                 335
Ser Ala Asn Gly Ala Tyr Gly Val Lys Gly Phe Ser Phe Lys Tyr Gly
            340                 345                 350
Asn Gly Val Trp Ile Gly Arg Thr Lys Ser Thr Asn Ser Arg Ser Gly
        355                 360                 365
Phe Glu Met Ile Trp Asp Pro Asn Gly Trp Thr Glu Thr Asp Ser Ser
    370                 375                 380
Phe Ser Val Lys Gln Asp Ile Val Ala Ile Thr Asp Trp Ser Gly Tyr
385                 390                 395                 400
Ser Gly Ser Phe Val Gln His Pro Glu Leu Thr Gly Leu Asp Cys Ile
                405                 410                 415
Arg Pro Cys Phe Trp Val Glu Leu Ile Arg Gly Arg Pro Lys Glu Ser
            420                 425                 430
Thr Ile Trp Thr Ser Gly Ser Ser Ile Ser Phe Cys Gly Val Asn Ser
        435                 440                 445
Asp Thr Val Ser Trp Ser Trp Pro Asp Gly Ala Glu Leu Pro Phe Thr
    450                 455                 460
Ile Asp Lys Tyr Pro Tyr Asp Val Pro Asp Tyr Ala
465                 470                 475

<210> SEQ ID NO 5
<211> LENGTH: 875
<212> TYPE: DNA
<213> ORGANISM: Artificial Sequence
<220> FEATURE:
<223> OTHER INFORMATION: Influenza H1N1&H5N1 M1 consensus sequence

<400> SEQUENCE: 5
ggtaccggat ccgccaccat ggactggacc tggattctgt tcctggtggc cgctgccacc      60
cgggtgcaca gcatgagcct gctgaccgag gtggagacct acgtgctgtc catcatcccc     120
agcggccctc tgaaggccga gatcgcccag cggctggaag atgtgttcgc cggcaagaac     180
accgacctgg aagccctgat ggaatggctg aaaacccggc ccatcctgag cccccctgacc    240 aagggcatcc tgggcttcgt gttcacccct accgtgccca gcgagcgggg cctgcagcgg     300
cggagattcg tgcagaacgc cctgaacggc aacggcgacc caacaacat ggaccgggcc      360 gtgaagctgt acaagaagct gaagcgggag atcaccttcc acggcgccaa agaggtggcc     420
ctgagctaca gcacaggcgc cctggccagc tgcatgggcc tgatctacaa ccggatgggc     480
accgtgacca ccgaggtggc cttcggcctg gtgtgcgcca cctgcgagca gatcgccgac     540
agccagcaca tcccaccg gcagatggcc accaccacca cccctgat ccggcacgag       600 aaccggatgg tcctggcctc caccaccgcc aaggccatgg aacagatggc cggcagcagc     660
gagcaggccg ccgaagccat ggaagtggcc agccaggcca gcagatggt gcaggccatg      720 cggaccatcg gcacccaccc cagcagcagc gccggactgc gggacgacct gctggaaaac     780
ctgcaggcct accagaaacg gatgggcgtg cagatgcagc ggttcaagta ccctacgac      840 gtgcccgact acgcctgatg agcggccgcg agctc                                875

<210> SEQ ID NO 6
<211> LENGTH: 279
```

```
<212> TYPE: PRT
<213> ORGANISM: Artificial Sequence
<220> FEATURE:
<223> OTHER INFORMATION: Influenza H1N1&H5N1 M1 consensus sequence

<400> SEQUENCE: 6

Met Asp Trp Thr Trp Ile Leu Phe Leu Val Ala Ala Thr Arg Val
1               5                   10                  15

His Ser Met Ser Leu Leu Thr Glu Val Glu Thr Tyr Val Leu Ser Ile
            20                  25                  30

Ile Pro Ser Gly Pro Leu Lys Ala Glu Ile Ala Gln Arg Leu Glu Asp
        35                  40                  45

Val Phe Ala Gly Lys Asn Thr Asp Leu Glu Ala Leu Met Glu Trp Leu
    50                  55                  60

Lys Thr Arg Pro Ile Leu Ser Pro Leu Thr Lys Gly Ile Leu Gly Phe
65                  70                  75                  80

Val Phe Thr Leu Thr Val Pro Ser Glu Arg Gly Leu Gln Arg Arg
                85                  90                  95

Phe Val Gln Asn Ala Leu Asn Gly Asn Gly Asp Pro Asn Asn Met Asp
                100                 105                 110

Arg Ala Val Lys Leu Tyr Lys Lys Leu Lys Arg Glu Ile Thr Phe His
            115                 120                 125

Gly Ala Lys Glu Val Ala Leu Ser Tyr Ser Thr Gly Ala Leu Ala Ser
        130                 135                 140

Cys Met Gly Leu Ile Tyr Asn Arg Met Gly Thr Val Thr Thr Glu Val
145                 150                 155                 160

Ala Phe Gly Leu Val Cys Ala Thr Cys Glu Gln Ile Ala Asp Ser Gln
                165                 170                 175

His Arg Ser His Arg Gln Met Ala Thr Thr Thr Asn Pro Leu Ile Arg
            180                 185                 190

His Glu Asn Arg Met Val Leu Ala Ser Thr Thr Ala Lys Ala Met Glu
        195                 200                 205

Gln Met Ala Gly Ser Ser Glu Gln Ala Ala Glu Ala Met Glu Val Ala
    210                 215                 220

Ser Gln Ala Arg Gln Met Val Gln Ala Met Arg Thr Ile Gly Thr His
225                 230                 235                 240

Pro Ser Ser Ser Ala Gly Leu Arg Asp Asp Leu Leu Glu Asn Leu Gln
                245                 250                 255

Ala Tyr Gln Lys Arg Met Gly Val Gln Met Gln Arg Phe Lys Tyr Pro
            260                 265                 270

Tyr Asp Val Pro Asp Tyr Ala
        275

<210> SEQ ID NO 7
<211> LENGTH: 1700
<212> TYPE: DNA
<213> ORGANISM: Artificial Sequence
<220> FEATURE:
<223> OTHER INFORMATION: Influenza H5N1 M2E-NP consensus sequence

<400> SEQUENCE: 7
ggtaccgaat cgccaccat ggactggacc tggatcctgt tcctggtcgc tgccgccacc       60
agggtgcaca gcagcctgct gaccgaggtg gagacccca cccggaacga gtggggctgc      120
cggtgcagcg acagcagcga ccggggcagg aagcggagaa gcgccagcca gggcaccaag      180
cggagctacg agcagatgga aacaggcggc gagcggcaga acgccaccga gatccgggcc      240
agcgtgggca gaatggtcgg cggcatcggc cggttctaca tccagatgtg caccgagctg      300
```

```
aagctgtccg actacgaggg ccggctgatc cagaacagca tcaccatcga gcggatggtg    360
ctgtccgcct tcgacgagcg gcggaacaga tacctggaag agcaccccag cgccggcaag    420
gaccccaaga aaaccggcgg acccatctac cggcggaggg acggcaagtg ggtgcgggag    480
ctgatcctgt acgacaaaga ggaaatccgg cggatctggc ggcaggccaa caacggcgag    540
gacgccacag ccggcctgac ccacctgatg atctggcaca gcaacctgaa cgacgccacc    600
taccagcgga caagggctct ggtccggacc ggcatggacc ccggatgtg cagcctgatg     660 cagggcagca cactgcccag aagaagcgga gccgctggcg cagccgtgaa gggcgtgggc    720
accatggtga tggaactgat ccggatgatc aagcggggca tcaacgaccg gaattttgg    780 aggggcgaga acggcaggcg gacccggatc gcctacgagc ggatgtgcaa catcctgaag    840
ggcaagttcc agacagccgc ccagcgggcc atgatggacc aggtccggga gagccggaac    900
cccggcaacg ccgagatcga ggacctgatc ttcctggcca gaagcgccct gatcctgcgg    960
ggcagcgtgg cccacaagag ctgcctgccc gcctgcgtgt acggactggc cgtggccagc    1020
ggctacgact tcgagcggga gggctacagc ctggtcggca tcgacccctt ccggctgctg    1080
cagaactccc aggtgttcag cctgatccgg cccaacgaga cccccgccca agtcccag     1140 ctggtctgga tggcctgcca gcgccgcc ttcgaggatc tgagagtgag cagcttcatc      1200
cggggcacca gagtggtgcc caggggccag ctgtccacca ggggcgtgca gatcgccagc    1260
aacgagaaca tggaagccat ggacagcaac accctggaac tgcggagccg gtactgggcc    1320
atccggacca gaagcggcgg caacaccaac cagcagcggg ccagcgccgg acagatcagc    1380
gtgcagccca ccttctccgt gcagcggaac ctgcccttcg agagggccac catcatggcc    1440
gccttcaccg caacaccgga gggccggacc agcgacatgc ggaccgagat catcaggatg    1500
atggaaagcg ccaggcccga ggacgtgagc ttccagggca ggggcgtgtt cgagctgtcc    1560
gatgagaagg ccaccaaccc catcgtgccc agcttcgaca tgaacaacga gggcagctac    1620
ttcttcggcg acaacgccga ggaatacgac aactacccct acgacgtgcc cgactacgcc    1680
tgatgagcgg ccgcgagctc                                                1700
```

<210> SEQ ID NO 8
<211> LENGTH: 554
<212> TYPE: PRT
<213> ORGANISM: Artificial Sequence
<220> FEATURE:
<223> OTHER INFORMATION: Influenza H5N1 M2E-NP consensus sequence

<400> SEQUENCE: 8

Met Asp Trp Thr Trp Ile Leu Phe Leu Val Ala Ala Ala Thr Arg Val
1               5                   10                  15

His Ser Ser Leu Leu Thr Glu Val Glu Thr Pro Thr Arg Asn Glu Trp
            20                  25                  30

Gly Cys Arg Cys Ser Asp Ser Ser Asp Arg Gly Arg Lys Arg Arg Ser
        35                  40                  45

Ala Ser Gln Gly Thr Lys Arg Ser Tyr Glu Gln Met Glu Thr Gly Gly
    50                  55                  60

Glu Arg Gln Asn Ala Thr Glu Ile Arg Ala Ser Val Gly Arg Met Val
65                  70                  75                  80

Gly Gly Ile Gly Arg Phe Tyr Ile Gln Met Cys Thr Glu Leu Lys Leu
                85                  90                  95

Ser Asp Tyr Glu Gly Arg Leu Ile Gln Asn Ser Ile Thr Ile Glu Arg
            100                 105                 110

-continued

```
Met Val Leu Ser Ala Phe Asp Glu Arg Arg Asn Arg Tyr Leu Glu Glu
            115                 120                 125

His Pro Ser Ala Gly Lys Asp Pro Lys Lys Thr Gly Gly Pro Ile Tyr
        130                 135                 140

Arg Arg Arg Asp Gly Lys Trp Val Arg Glu Leu Ile Leu Tyr Asp Lys
145                 150                 155                 160

Glu Glu Ile Arg Arg Ile Trp Arg Gln Ala Asn Asn Gly Glu Asp Ala
                165                 170                 175

Thr Ala Gly Leu Thr His Leu Met Ile Trp His Ser Asn Leu Asn Asp
            180                 185                 190

Ala Thr Tyr Gln Arg Thr Arg Ala Leu Val Arg Thr Gly Met Asp Pro
        195                 200                 205

Arg Met Cys Ser Leu Met Gln Gly Ser Thr Leu Pro Arg Arg Ser Gly
210                 215                 220

Ala Ala Gly Ala Ala Val Lys Gly Val Gly Thr Met Val Met Glu Leu
225                 230                 235                 240

Ile Arg Met Ile Lys Arg Gly Ile Asn Asp Arg Asn Phe Trp Arg Gly
                245                 250                 255

Glu Asn Gly Arg Arg Thr Arg Ile Ala Tyr Glu Arg Met Cys Asn Ile
            260                 265                 270

Leu Lys Gly Lys Phe Gln Thr Ala Ala Gln Arg Ala Met Met Asp Gln
        275                 280                 285

Val Arg Glu Ser Arg Asn Pro Gly Asn Ala Glu Ile Glu Asp Leu Ile
290                 295                 300

Phe Leu Ala Arg Ser Ala Leu Ile Leu Arg Gly Ser Val Ala His Lys
305                 310                 315                 320

Ser Cys Leu Pro Ala Cys Val Tyr Gly Leu Ala Val Ala Ser Gly Tyr
                325                 330                 335

Asp Phe Glu Arg Glu Gly Tyr Ser Leu Val Gly Ile Asp Pro Phe Arg
            340                 345                 350

Leu Leu Gln Asn Ser Gln Val Phe Ser Leu Ile Arg Pro Asn Glu Asn
        355                 360                 365

Pro Ala His Lys Ser Gln Leu Val Trp Met Ala Cys His Ser Ala Ala
370                 375                 380

Phe Glu Asp Leu Arg Val Ser Ser Phe Ile Arg Gly Thr Arg Val Val
385                 390                 395                 400

Pro Arg Gly Gln Leu Ser Thr Arg Gly Val Gln Ile Ala Ser Asn Glu
                405                 410                 415

Asn Met Glu Ala Met Asp Ser Asn Thr Leu Glu Leu Arg Ser Arg Tyr
            420                 425                 430

Trp Ala Ile Arg Thr Arg Ser Gly Gly Asn Thr Asn Gln Gln Arg Ala
        435                 440                 445

Ser Ala Gly Gln Ile Ser Val Gln Pro Thr Phe Ser Val Gln Arg Asn
450                 455                 460

Leu Pro Phe Glu Arg Ala Thr Ile Met Ala Ala Phe Thr Gly Asn Thr
465                 470                 475                 480

Glu Gly Arg Thr Ser Asp Met Arg Thr Glu Ile Ile Arg Met Met Glu
                485                 490                 495

Ser Ala Arg Pro Glu Asp Val Ser Phe Gln Gly Arg Gly Val Phe Glu
            500                 505                 510

Leu Ser Asp Glu Lys Ala Thr Asn Pro Ile Val Pro Ser Phe Asp Met
        515                 520                 525

Asn Asn Glu Gly Ser Tyr Phe Phe Gly Asp Asn Ala Glu Glu Tyr Asp
530                 535                 540
```

Asn Tyr Pro Tyr Asp Val Pro Asp Tyr Ala
545                 550

<210> SEQ ID NO 9
<211> LENGTH: 1728
<212> TYPE: DNA
<213> ORGANISM: Artificial Sequence
<220> FEATURE:
<223> OTHER INFORMATION: Influenza H1 consensu sequence

<400> SEQUENCE: 9

```
ggtaccaagc ttgccaccat gaaggtgaaa ctgctggtgc tgctgtgcac cttcaccgcc      60
acctacgccg acaccatctg catcggctac acgccaaca acagcaccga caccgtggat     120
accgtgctgg aaaagaacgt gaccgtgacc cacagcgtga acctgctgga agatagccac     180
aacggcaagc tgtgcctgct gaaaggcatc gcccccctgc agctgggcaa ctgcagcgtg     240
gccggctgga tcctgggcaa ccccgagtgc gagctgctga tttccaaaga agctggtcc      300
tacatcgtgg agaccccaa ccccgagaac ggcacctgct accccggcta cttcgccgac     360
tacgaggaac tgcgggagca gctgtccagc gtgagcagct cgagcggtt cgagatcttc      420
cccaaagaga gcagctggcc caaccacacc gtgaccggcg tgagcgccag ctgctcccac      480
aatggcaaga gcagcttcta ccggaacctg ctgtggctga ccggcaagaa cggcctgtac      540
cccaacctga gcaagagcta cgccaataac aaagaaaagg aagtgctggt gctgtggggc     600
gtgcaccacc cccccaacat cggcgaccag cgggccctgt accacaccga aacgcctac      660
gtgagcgtgg tgtccagcca ctacagccgg cggttcaccc ccgagatcgc caagcggccc     720
aaagtgcggg accaggaagg ccggatcaac tactactgga ccctgctgga accgggcgac     780
accatcatct tcgaggccaa cggcaacctg atcgccccca gatacgcctt cgccctgagc     840
cggggcttcg gcagcggcat catcaccagc aacgcccca tggacgagtg cgacgccaag     900
tgccagaccc ctcagggagc tattaacagc agcctgccct tccagaacgt gcaccccgtg     960
accatcggcg agtgccccaa gtacgtgcgg agcgccaagc tgcggatggt gaccggcctg    1020
cggaacatcc ccagcatcca gagcaggggc ctgttcggcg ccatcgccgg cttcatcgag    1080
ggcggctgga ccggcatggt ggacgggtgg tacggctacc accaccagaa cgagcagggc    1140
agcggctacg ccgccgacca aagagcacc cagaacgcca tcaacggcat caccaacaag    1200
gtgaacagcg tgatcgagaa gatgaacacc cagttcaccg ccgtgggcaa agagttcaac    1260
aagctggaac ggcggatgga aaacctgaac aagaaggtgg acgacggctt cctggacatc    1320
tggacctaca acgccgagct gctggtgctg ctggaaaacg agcggaccct ggacttccac    1380
gacagcaacg tgaagaacct gtacgagaag gtgaaaagcc agctgaagaa caacgccaaa    1440
gagatcggca acggctgctt cgagttctac cacaagtgca acgacgagtg catggaaagc    1500
gtgaagaatg gcacctacga ctaccccaag tacagcgagg aaagcaagct gaaccgggag    1560
aagatcgacg gcgtgaagct ggaaagcatg ggcgtgtacc agatcctggc catctacagc    1620
accgtcgctt ccagcctcgt cctgctcgtg tccctgggcg ccatctcctt ttggatgtgc    1680
agcaacggca gcctgcagtg ccggatctgc atctgatgac tcgagctc                 1728
```

<210> SEQ ID NO 10
<211> LENGTH: 565
<212> TYPE: PRT
<213> ORGANISM: Artificial Sequence
<220> FEATURE:
<223> OTHER INFORMATION: Influenza H1 consensus sequence

<400> SEQUENCE: 10

```
Met Lys Val Lys Leu Leu Val Leu Leu Cys Thr Phe Thr Ala Thr Tyr
1               5                   10                  15
Ala Asp Thr Ile Cys Ile Gly Tyr His Ala Asn Asn Ser Thr Asp Thr
            20                  25                  30
Val Asp Thr Val Leu Glu Lys Asn Val Thr Val Thr His Ser Val Asn
        35                  40                  45
Leu Leu Glu Asp Ser His Asn Gly Lys Leu Cys Leu Leu Lys Gly Ile
    50                  55                  60
Ala Pro Leu Gln Leu Gly Asn Cys Ser Val Ala Gly Trp Ile Leu Gly
65                  70                  75                  80
Asn Pro Glu Cys Glu Leu Leu Ile Ser Lys Glu Ser Trp Ser Tyr Ile
                85                  90                  95
Val Glu Thr Pro Asn Pro Glu Asn Gly Thr Cys Tyr Pro Gly Tyr Phe
            100                 105                 110
Ala Asp Tyr Glu Glu Leu Arg Glu Gln Leu Ser Ser Val Ser Ser Phe
        115                 120                 125
Glu Arg Phe Glu Ile Phe Pro Lys Glu Ser Ser Trp Pro Asn His Thr
    130                 135                 140
Val Thr Gly Val Ser Ala Ser Cys Ser His Asn Gly Lys Ser Ser Phe
145                 150                 155                 160
Tyr Arg Asn Leu Leu Trp Leu Thr Gly Lys Asn Gly Leu Tyr Pro Asn
                165                 170                 175
Leu Ser Lys Ser Tyr Ala Asn Asn Lys Glu Lys Glu Val Leu Val Leu
            180                 185                 190
Trp Gly Val His His Pro Pro Asn Ile Gly Asp Gln Arg Ala Leu Tyr
        195                 200                 205
His Thr Glu Asn Ala Tyr Val Ser Val Val Ser Ser His Tyr Ser Arg
    210                 215                 220
Arg Phe Thr Pro Glu Ile Ala Lys Arg Pro Lys Val Arg Asp Gln Glu
225                 230                 235                 240
Gly Arg Ile Asn Tyr Tyr Trp Thr Leu Leu Glu Pro Gly Asp Thr Ile
                245                 250                 255
Ile Phe Glu Ala Asn Gly Asn Leu Ile Ala Pro Arg Tyr Ala Phe Ala
            260                 265                 270
Leu Ser Arg Gly Phe Gly Ser Gly Ile Ile Thr Ser Asn Ala Pro Met
        275                 280                 285
Asp Glu Cys Asp Ala Lys Cys Gln Thr Pro Gln Gly Ala Ile Asn Ser
    290                 295                 300
Ser Leu Pro Phe Gln Asn Val His Pro Val Thr Ile Gly Glu Cys Pro
305                 310                 315                 320
Lys Tyr Val Arg Ser Ala Lys Leu Arg Met Val Thr Gly Leu Arg Asn
                325                 330                 335
Ile Pro Ser Ile Gln Ser Arg Gly Leu Phe Gly Ala Ile Ala Gly Phe
            340                 345                 350
Ile Glu Gly Gly Trp Thr Gly Met Val Asp Gly Trp Tyr Gly Tyr His
        355                 360                 365
His Gln Asn Glu Gln Gly Ser Gly Tyr Ala Ala Asp Gln Lys Ser Thr
    370                 375                 380
Gln Asn Ala Ile Asn Gly Ile Thr Asn Lys Val Asn Ser Val Ile Glu
385                 390                 395                 400
Lys Met Asn Thr Gln Phe Thr Ala Val Gly Lys Glu Phe Asn Lys Leu
                405                 410                 415
```

```
Glu Arg Arg Met Glu Asn Leu Asn Lys Lys Val Asp Asp Gly Phe Leu
            420                 425                 430
Asp Ile Trp Thr Tyr Asn Ala Glu Leu Leu Val Leu Leu Glu Asn Glu
                435                 440                 445
Arg Thr Leu Asp Phe His Asp Ser Asn Val Lys Asn Leu Tyr Glu Lys
            450                 455                 460
Val Lys Ser Gln Leu Lys Asn Asn Ala Lys Glu Ile Gly Asn Gly Cys
465                 470                 475                 480
Phe Glu Phe Tyr His Lys Cys Asn Asp Glu Cys Met Glu Ser Val Lys
                485                 490                 495
Asn Gly Thr Tyr Asp Tyr Pro Lys Tyr Ser Glu Ser Lys Leu Asn
            500                 505                 510
Arg Glu Lys Ile Asp Gly Val Lys Leu Glu Ser Met Gly Val Tyr Gln
            515                 520                 525
Ile Leu Ala Ile Tyr Ser Thr Val Ala Ser Ser Leu Val Leu Leu Val
            530                 535                 540
Ser Leu Gly Ala Ile Ser Phe Trp Met Cys Ser Asn Gly Ser Leu Gln
545                 550                 555                 560
Cys Arg Ile Cys Ile
            565

<210> SEQ ID NO 11
<211> LENGTH: 1731
<212> TYPE: DNA
<213> ORGANISM: Artificial Sequence
<220> FEATURE:
<223> OTHER INFORMATION: Influenza H3 consensus sequence

<400> SEQUENCE: 11
ggtaccaagc ttgccaccat gaaaaccatc atcgccctga ctacatcct gtgcctggtg      60 ttcgcccaga gctgcccgg caacgacaac agcaccgcca ccctgtgtct gggccaccac    120
gccgtgccca acggcaccat cgtgaaaaca atcaccaacg accagatcga ggtgaccaac    180
gccaccgagc tggtgcagag cagcagcacc ggcggcatct gcacagcccc caccagatc    240 ctggacggcg agaactgcac cctgatcgac gccctgctgg gcgaccctca gtgcgacggc    300
ttccagaaca aaagtggga cctgttcgtg gagcggagca aggcctacag caactgctac    360
ccctacgacg tgcccgacta cgccagcctg cggagcctgg tggccagcag cggcaccctg    420
gaattcaaca cgagagctt caactggacc ggcgtgaccc agaacggcac cagcagcgcc    480
tgcaagcggc ggagcaacaa cagcttcttt tccagactga actggctgac ccacctgaag    540
ttcaagtacc ccgccctgaa cgtgaccatg ccaacaatg agaagttcga caagctgtac    600
atctggggcg tgcaccaccc cggcaccgac aatgaccaga tcagcctgta cgcccaggcc    660
agcggccgga tcaccgtgag caccaagcgg agccagcaga ccgtgatccc caacatcggc    720
agccggccca gagtgagaga catccccagc cggatcagca tctactggac aatcgtgaag    780
cccggcgaca tcctgctgat caactccacc ggcaacctga tcgcccccag ggctacttc    840 aagatcagaa gcggcaagag cagcatcatg cggagcgacg ccccatcgg caagtgcaac    900 agcgagtgca tcaccccaa tggcagcatc cccaacgaca gcccttcca gaacgtgaac    960 cggatcaccc tacggcgctg ccccagatac gtgaagcaga cacccctgaa gctggccacc   1020
ggcatgcgga acgtgcccga aagcagacc cggggcatct tcggcgccat cgccggcttc   1080
atcgagaacg gctgggaggg catggtggac ggtggtacg gcttccggca ccagaactcc   1140
gagggcatcg gccaggccgc cgacctgaag agcacccagg ccgccatcaa ccagatcaac   1200
```

```
ggcaagctga accggctgat cggcaagacc aacgagaagt tccaccagat cgaaaagaa    1260 ttcagcgagg tggagggccg gatccaggac ctggaaaagt acgtggagga caccaagatc    1320
gacctgtgga gctacaacgc cgagctgctg gtcgccctgg aaaaccagca ccatcgac     1380 ctgaccgaca gcgagatgaa caagctgttc gagcggacca agaagcagct gcgggagaac    1440
gccgaggaca tgggcaacgg ctgctttaag atctaccaca gtgcgacaa cgcctgcatc     1500 ggcagcatcc ggaacggcac ctacgaccac gacgtgtacc gggacgaggc cctgaacaac    1560
cggttccaga tcaagggcgt ggagctgaag agcggctaca aggactggat cctgtggatc    1620
agcttcgcca tcagctgctt tctgctgtgc gtggccctgc tgggattcat catgtgggcc    1680
tgccagaagg gcaacatccg ctgcaacatc tgcatctgat gactcgagct c            1731

<210> SEQ ID NO 12
<211> LENGTH: 566
<212> TYPE: PRT
<213> ORGANISM: Artificial Sequence
<220> FEATURE:
<223> OTHER INFORMATION: Influenza H3 consensus sequence

<400> SEQUENCE: 12

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Ser Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
```

```
                275                 280                 285
Pro Ile Gly Lys Cys Asn Ser Glu Cys Ile Thr Pro Asn Gly Ser Ile
        290                 295                 300
Pro Asn Asp Lys Pro Phe Gln Asn Val Asn Arg Ile Thr Tyr Gly Ala
305                 310                 315                 320
Cys Pro Arg Tyr Val Lys Gln Asn Thr Leu Lys Leu Ala Thr Gly Met
                325                 330                 335
Arg Asn Val Pro Glu Lys Gln Thr Arg Gly Ile Phe Gly Ala Ile Ala
            340                 345                 350
Gly Phe Ile Glu Asn Gly Trp Glu Gly Met Val Asp Gly Trp Tyr Gly
        355                 360                 365
Phe Arg His Gln Asn Ser Glu Gly Ile Gly Gln Ala Ala Asp Leu Lys
    370                 375                 380
Ser Thr Gln Ala Ala Ile Asn Gln Ile Asn Gly Lys Leu Asn Arg Leu
385                 390                 395                 400
Ile Gly Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
        435                 440                 445
Asn Gln His Thr Ile Asp Leu Thr Asp Ser Glu Met Asn Lys Leu Phe
    450                 455                 460
Glu Arg Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
            500                 505                 510
Asn Asn Arg Phe Gln Ile Lys Gly Val Glu Leu Lys Ser Gly Tyr Lys
        515                 520                 525
Asp Trp Ile Leu Trp Ile Ser Phe Ala Ile Ser Cys Phe Leu Leu Cys
    530                 535                 540
Val Ala Leu Leu Gly Phe Ile Met Trp Ala Cys Gln Lys Gly Asn Ile
545                 550                 555                 560
Arg Cys Asn Ile Cys Ile
                565

<210> SEQ ID NO 13
<211> LENGTH: 1791
<212> TYPE: DNA
<213> ORGANISM: Artificial Sequence
<220> FEATURE:
<223> OTHER INFORMATION: Influenza H5 consensus sequence

<400> SEQUENCE: 13
atggactgga cctggatcct gttcctggtg ccgctgcca cccgggtgca cagcatggaa      60
aagatcgtgc tgctgttcgc catcgtgagc ctggtgaaga cgaccagat ctgcatcggc     120 taccacgcca acaacagcac cgagcaggtg acaccatca tggaaaaaaa cgtgaccgtg     180
acccacgccc aggacatcct ggaaaagacc cacaacggca gctgtgcga cctggacggc     240 gtgaagcccc tgatcctgcg ggactgcagc gtggccggct ggctgctggg caaccccatg     300
tgcgacgagt tcatcaacgt gcccgagtgg agctacatcg tggagaaggc caaccccgtg     360
aacgacctgt gctaccccgg cgacttcaac gactacgagg aactgaagca cctgctgtcc     420
```

-continued

```
cggatcaacc acttcgagaa gatccagatc atccccaaga gcagctggtc cagccacgag    480
gccagcctgg gcgtgagcag cgcctgccca taccagggca agtccagctt cttccggaac    540
gtggtgtggc tgatcaagaa gaacagcacc taccccacca tcaagcggag ctacaacaac    600
accaaccagg aagatctgct ggtcctgtgg ggcatccacc accccaacga cgccgccgag    660
cagaccaagc tgtaccagaa ccccaccacc tacatcagcg tgggcaccag caccctgaac    720
cagcggctgg tgccccggat cgccacccgg tccaaggtga acggccagag cggccggatg    780
gaattcttct ggaccatcct gaagcccaac gatgccatca acttcgagag caacggcaac    840
ttcatcgccc ccgagtacgc ctacaagatc gtgaagaagg gcgacagcac catcatgaag    900
agcgagctgg aatacggcaa ctgcaacacc aagtgccaga cccccatggg cgccatcaac    960
agcagcatgc ccttccacaa catccacccc ctgaccatcg gcgagtgccc caagtacgtg   1020
aagagcaaca ggctggtgct ggccaccggc ctgcggaaca gcccccagcg ggagcggcgg   1080
aggaagaagc ggggcctgtt cggcgccatc gccggcttca tcgagggcgg ctggcagggc   1140
atggtggacg ggtggtacgg ctaccaccac agcaatgagc agggcagcgg ctacgccgcc   1200
gacaaagaga gcacccagaa ggccatcgac ggcgtcacca acaaggtgaa cagcatcatc   1260
gacaagatga acacccagtt cgaggccgtg ggccgggagt tcaacaacct ggaacggcgg   1320
atcgagaacc tgaacaagaa aatggaagat ggcttcctgg acgtgtggac ctacaacgcc   1380
gagctgctgg tgctgatgga aaacgagcgg accctggact tccacgacag caacgtgaag   1440
aacctgtacg acaaagtgcg gctgcagctg cgggacaacg ccaaagagct gggcaacggc   1500
tgcttcgagt tctaccacaa gtgcgacaac gagtgcatgg aaagcgtgcg gaacggcacc   1560
tacgactacc cccagtacag cgaggaagcc cggctgaagc gggaggaaat cagcggcgtg   1620
aaactggaaa gcatcggcat ctaccagatc ctgagcatct acagcaccgt ggccagcagc   1680
ctggccctgg ccatcatggt ggccggcctg agcctgtgga tgtgcagcaa cggcagcctg   1740
cagtgccgga tctgcatcta cccctacgac gtgcccgact acgcctgatg a            1791
```

```

<210> SEQ ID NO 14
<211> LENGTH: 579
<212> TYPE: PRT
<213> ORGANISM: Artificial Sequence
<220> FEATURE:
<223> OTHER INFORMATION: Influenza HA consensus sequence

<400> SEQUENCE: 14

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125
```

```
Lys Ile Gln Ile Ile Pro Lys Ser Ser Trp Ser Ser His Glu Ala Ser
            130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
            195                 200                 205

Asn Pro Thr Thr Tyr Ile Ser Val Gly Thr Ser Thr Leu Asn Gln Arg
210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
            275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
            515                 520                 525

Ile Tyr Gln Ile Leu Ser Ile Tyr Ser Thr Val Ala Ser Ser Leu Ala
530                 535                 540

Leu Ala Ile Met Val Ala Gly Leu Ser Leu Trp Met Cys Ser Asn Gly
545                 550                 555                 560
```

```
Ser Leu Gln Cys Arg Ile Cys Ile Tyr Pro Tyr Asp Val Pro Asp Tyr
            565                 570                 575

Ala Leu Glu

<210> SEQ ID NO 15
<211> LENGTH: 4733
<212> TYPE: DNA
<213> ORGANISM: Artificial Sequence
<220> FEATURE:
<223> OTHER INFORMATION: DNA plasma having encoding sequence for
      influenza consensus H5N1 HA

<400> SEQUENCE: 15
gctgcttcgc gatgtacggg ccagatatac gcgttgacat tgattattga ctagttatta      60
atagtaatca attacggggt cattagttca tagcccatat atggagttcc gcgttacata     120
acttacggta atggcccgc ctggctgacc gcccaacgac ccccgcccat tgacgtcaat      180
aatgacgtat gttcccatag taacgccaat agggactttc cattgacgtc aatgggtgga    240
gtatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgccacca tggactggac ctggatcctg ttcctggtgg ccgctgccac ccgggtgcac    780
agcatggaaa agatcgtgct gctgttcgcc atcgtgagcc tggtgaagag cgaccagatc    840
tgcatcggct accacgccaa caacagcacc gagcaggtgg acaccatcat ggaaaaaaac    900
gtgaccgtga cccacgccca ggacatcctg gaaaagaccc acaacggcaa gctgtgcgac    960
ctggacggcg tgaagccct gatcctgcgg gactgcagcg tggccggctg gctgctgggc    1020
aaccccatgt gcgacgagtt catcaacgtg cccgagtgga gctacatcgt ggagaaggcc    1080
aaccccgtga acgacctgtg ctaccccggc gacttcaacg actacgagga actgaagcac    1140
ctgctgtccc ggatcaacca cttcgagaag atccagatca tccccaagag cagctggtcc    1200
agccacgagg ccagcctggg cgtgagcagc gcctgcccat accagggcaa gtccagcttc    1260
ttccggaacg tggtgtggct gatcaagaag aacagcacct accccaccat caagcggagc    1320
tacaacaaca ccaaccagga agatctgctg gtcctgtggg gcatccacca ccccaacgac    1380
gccgccgagc agaccaagct gtaccagaac ccaccaccct catcagcgt gggcaccagc    1440 accctgaacc agcggctggt gcccggatc gccacccggt ccaaggtgaa cggccagagc    1500
ggccggatgg aattcttctg gaccatcctg aagcccaacg atgccatcaa cttcgagagc    1560
aacggcaact tcatcgcccc cgagtacgcc tacaagatcg tgaagaaggg cgacagcacc    1620
atcatgaaga gcgagctgga atacggcaac tgcaacacca gtgccagac ccccatgggc    1680 gccatcaaca gcagcatgcc cttccacaac atccacccc tgaccatcgg cgagtgcccc    1740
aagtacgtga agagcaacag gctggtgctg gccaccggcc tgcggaacag ccccagcgg    1800 gagcggcgga ggaagaagcg gggcctgttc ggcgccatcg ccggcttcat cgagggcggc    1860
tggcagggca tggtggacgg cgtggtacgg caccaccaca gcaatgagca gggcagcggc    1920
```

```
tacgccgccg acaaagagag cacccagaag gccatcgacg gcgtcaccaa caaggtgaac    1980
agcatcatcg acaagatgaa cacccagttc gaggccgtgg gccgggagtt caacaacctg    2040
gaacggcgga tcgagaacct gaacaagaaa atggaagatg gcttcctgga cgtgtggacc    2100
tacaacgccg agctgctggt gctgatggaa acgagcgga ccctggactt ccacgacagc    2160
aacgtgaaga acctgtacga caaagtgcgg ctgcagctgc gggacaacgc caaagagctg    2220
ggcaacggct gcttcgagtt ctaccacaag tgcgacaacg agtgcatgga aagcgtgcgg    2280
aacggcacct acgactaccc ccagtacagc gaggaagccc ggctgaagcg ggaggaaatc    2340
agcggcgtga aactggaaag catcggcatc taccagatcc tgagcatcta cagcaccgtg    2400
gccagcagcc tggccctggc catcatggtg gccggcctga gctgtggat gtgcagcaac    2460 ggcagcctgc agtgccggat ctgcatctac ccctacgacg tgcccgacta cgcctgatga    2520
ctcgagtcta gagggcccgt ttaaacccgc tgatcagcct cgactgtgcc ttctagttgc    2580
cagccatctg ttgtttgccc ctcccccgtg ccttccttga ccctggaagg tgccactccc    2640
actgtccttt cctaataaaa tgaggaaatt gcatcgcatt gtctgagtag gtgtcattct    2700
attctggggg gtggggtggg gcaggacagc aaggggggagg attgggaaga caatagcagg    2760
catgctgggg atgcggtggg ctctatggct tctactgggc ggttttatgg acagcaagcg    2820
aaccggaatt gccagctggg gcgccctctg gtaaggttgg gaagccctgc aaagtaaact    2880
ggatggcttt cttgccgcca aggatctgat ggcgcagggg atcaagctct gatcaagaga    2940
caggatgagg atcgtttcgc atgattgaac aagatggatt gcacgcaggt tctccggccg    3000
cttgggtgga gaggctattc ggctatgact gggcacaaca gacaatcggc tgctctgatg    3060
ccgccgtgtt ccggctgtca gcgcaggggc gcccggttct ttttgtcaag accgacctgt    3120
ccggtgccct gaatgaactg caagacgagg cagcgcggct atcgtggctg gccacgacgg    3180
gcgttccttg cgcagctgtg ctcgacgttg tcactgaagc gggaagggac tggctgctat    3240
tgggcgaagt gccggggcag gatctcctgt catctcacct tgctcctgcc gagaaagtat    3300
ccatcatggc tgatgcaatg cggcggctgc atacgcttga tccggctacc tgcccattcg    3360
accaccaagc gaaacatcgc atcgagcgag cacgtactcg gatggaagcc ggtcttgtcg    3420
atcaggatga tctggacgaa gagcatcagg ggctcgcgcc agccgaactg ttcgccaggc    3480
tcaaggcgag catgcccgac ggcgaggatc tcgtcgtgac ccatggcgat gcctgcttgc    3540
cgaatatcat ggtggaaaat ggccgctttt ctggattcat cgactgtggc cggctgggtg    3600
tggcggaccg ctatcaggac atagcgttgg ctacccgtga tattgctgaa gagcttggcg    3660
gcgaatgggc tgaccgcttc ctcgtgcttt acggtatcgc cgctcccgat tcgcagcgca    3720
tcgccttcta tcgccttctt gacgagttct tctgaattat taacgcttac aatttcctga    3780
tgcggtattt tctccttacg catctgtgcg gtatttcaca ccgcatcagg tggcactttt    3840
cggggaaatg tgcgcggaac ccctatttgt ttatttttct aaatacattc aaatatgtat    3900
ccgctcatga caataaacc ctgataaatg cttcaataat agcacgtgct aaaacttcat    3960
ttttaattta aaaggatcta ggtgaagatc cttttgata atctcatgac caaaatccct    4020
taacgtgagt tttcgttcca ctgagcgtca gaccccgtag aaaagatcaa aggatcttct    4080
tgagatcctt ttttctgcg cgtaatctgc tgcttgcaaa caaaaaaacc accgctacca    4140
gcggtggttt gtttgccgga tcaagagcta ccaactcttt ttccgaaggt aactggcttc    4200
agcagagcgc agataccaaa tactgttctt ctagtgtagc cgtagttagg ccaccacttc    4260
aagaactctg tagcaccgcc tacatacctc gctctgctaa tcctgttacc agtggctgct    4320
```

-continued gccagtggcg ataagtcgtg tcttaccggg ttggactcaa gacgatagtt accggataag 4380
gcgcagcggt cgggctgaac ggggggttcg tgcacacagc ccagcttgga gcgaacgacc 4440
tacaccgaac tgagatacct acagcgtgag ctatgagaaa gcgccacgct tcccgaaggg 4500
agaaaggcgg acaggtatcc ggtaagcggc agggtcggaa caggagagcg cacgagggag 4560
cttccagggg gaaacgcctg gtatctttat agtcctgtcg ggtttcgcca cctctgactt 4620
gagcgtcgat ttttgtgatg ctcgtcaggg gggcggagcc tatggaaaaa cgccagcaac 4680
gcggcctttt tacggttcct ggccttttgc tggccttttg ctcacatgtt ctt 4733

<210> SEQ ID NO 16
<211> LENGTH: 4418
<212> TYPE: DNA
<213> ORGANISM: Artificial Sequence
<220> FEATURE:
<223> OTHER INFORMATION: DNA plasmas having encoding sequence for influenza consensus NA

<400> SEQUENCE: 16
gctgcttcgc gatgtacggg ccagatatac gcgttgacat tgattattga ctagttatta 60
atagtaatca attacggggt cattagttca tagcccatat atggagttcc gcgttacata 120
acttacggta aatggcccgc ctggctgacc gcccaacgac ccccgcccat tgacgtcaat 180
aatgacgtat gttcccatag taacgccaat agggactttc cattgacgtc aatgggtgga 240
gtatttacgg taaactgccc acttggcagt acatcaagtg tatcatatgc caagtacgcc 300
ccctattgac gtcaatgacg gtaaatggcc cgcctggcat tatgcccagt acatgacctt 360
atgggacttt cctacttggc agtacatcta cgtattagtc atcgctatta ccatggtgat 420
gcggttttgg cagtacatca atgggcgtgg atagcggttt gactcacggg gatttccaag 480
tctccacccc attgacgtca atgggagttt gttttggcac caaaatcaac gggactttcc 540
aaaatgtcgt aacaactccg ccccattgac gcaaatgggc ggtaggcgtg tacggtggga 600
ggtctatata agcagagctc tctggctaac tagagaaccc actgcttact ggcttatcga 660
aattaatacg actcactata gggagaccca agctggctag cgtttaaact taagcttggt 720
accgagctcg gatccactag tccagtgtgg tggaattcgc caccatggac tggacctgga 780
tcctgttcct ggtggccgct gccacccggg tgcacagcat gaaccccaac cagaagatca 840
tcaccatcgg cagcatctgc atggtgatcg gcatcgtgag cctgatgctg cagatcggca 900
acatgatcag catctgggtg tcccacagca tccagaccgg caaccagcac caggccgagc 960
ccatcagcaa caccaacttt ctgaccgaga aggccgtggc cagcgtgacc ctggccggca 1020
acagcagcct gtgccccatc agcggctggg ccgtgtacag caaggacaac agcatccgga 1080
tcggcagcaa gggcgacgtg ttcgtgatcc gggagccctt catcagctgc agccacctgg 1140
aatgccggac cttcttcctg acccaggggg ccctgctgaa cgacaagcac agcaacggca 1200
ccgtgaagga cagaagcccc taccggaccc tgatgagctg ccccgtgggc gaggccccca 1260
gcccctacaa cagccggttc gagagcgtgg cctggtccgc cagcgcctgc cacgacggca 1320
ccagctggct gaccatcggc atcagcggcc ctgacaacgg cgccgtggcc gtgctgaagt 1380
acaacggcat catcaccgac accatcaaga gctggcggaa caacatcctg cggacccagg 1440
aaagcgagtg cgcctgcgtg aacggcagct gcttcaccgt gatgaccgac ggccccagca 1500
acggccaggc cagctacaag atcttcaaga tggaaaaggg caaggtggtg aagagcgtgg 1560
agctggacgc ccccaactac cactacgagg aatgcagctg ctaccccgac gccggcgaga 1620

-continued

```
tcacctgcgt gtgccgggac aactggcacg gcagcaaccg gccctgggtg tccttcaacc    1680
agaacctgga ataccagatc ggctacatct gcagcggcgt gttcggcgac aaccccaggc    1740
ccaacgatgg caccggcagc tgcggccctg tgagcgccaa cggcgcctac ggcgtgaagg    1800
gcttcagctt caagtacggc aacggcgtgt ggatcggccg gaccaagagc accaacagca    1860
gatccggctt cgagatgatc tgggaccccA acggctggac cgagaccgac agcagcttca    1920
gcgtgaagca ggacatcgtg gccatcaccg actggtccgg ctacagcggc agcttcgtgc    1980
agcaccccga gctgaccggc ctggactgca tccggccctg cttttgggtg gagctgatca    2040
gaggcaggcc caaagagagc accatctgga ccagcggcag cagcatcagc ttttgcggcg    2100
tgaacagcga caccgtgagc tggtcctggc ccgacggcgc cgagctgccc ttcaccatcg    2160
acaagtaccc ctacgacgtg cccgactacg cctgatgagc ggccgctcga gtctagaggg    2220
cccgtttaaa cccgctgatc agcctcgact gtgccttcta gttgccagcc atctgttgtt    2280
tgcccctccc ccgtgccttc cttgaccctg gaaggtgcca ctcccactgt cctttcctaa    2340
taaaatgagg aaattgcatc gcattgtctg agtaggtgtc attctattct ggggggtggg    2400
gtggggcagg acagcaaggg ggaggattgg gaagacaata gcaggcatgc tggggatgcg    2460
gtgggctcta tggcttctac tgggcggttt tatggacagc aagcgaaccg gaattgccag    2520
ctggggcgcc ctctggtaag gttgggaagc cctgcaaagt aaactggatg gctttcttgc    2580
cgccaaggat ctgatggcgc aggggatcaa gctctgatca agagacagga tgaggatcgt    2640
ttcgcatgat tgaacaagat ggattgcacg caggttctcc ggccgcttgg gtggagaggc    2700
tattcggcta tgactgggca acagacaa tcggctgctc tgatgccgcc gtgttccggc    2760
tgtcagcgca gggggcgccg gttcttttg tcaagaccga cctgtccggt gccctgaatg    2820
aactgcaaga cgaggcagcg cggctatcgt ggctggccac gacgggcgtt ccttgcgcag    2880
ctgtgctcga cgttgtcact gaagcgggaa gggactggct gctattgggc gaagtgccgg    2940
ggcaggatct cctgtcatct caccttgctc ctgccgagaa agtatccatc atggctgatg    3000
caatgcggcg gctgcatacg cttgatccgg ctacctgccc attcgaccac caagcgaaac    3060
atcgcatcga gcgagcacgt actcggatgg aagccggtct tgtcgatcag gatgatctgg    3120
acgaagagca tcaggggctc gcgccagccg aactgttcgc caggctcaag gcgagcatgc    3180
ccgacggcga ggatctcgtc gtgacccatg gcgatgcctg cttgccgaat atcatggtgg    3240
aaaatggccg cttttctgga ttcatcgact gtggccggct gggtgtggcg accgctatc    3300 aggacatagc gttggctacc cgtgatattg ctgaagagct tggcggcgaa tgggctgacc    3360
gcttcctcgt gctttacggt atcgccgctc ccgattcgca gcgcatcgcc ttctatcgcc    3420
ttcttgacga gttcttctga attattaacg cttacaattt cctgatgcgg tatttctcc    3480 ttacgcatct gtgcggtatt tcacaccgca tcaggtggca cttttcgggg aaatgtgcgc    3540 ggaacccta tttgtttatt tttctaaata cattcaaata tgtatccgct catgagacaa    3600
taaccctgat aaatgcttca ataatagcac gtgctaaaac ttcattttta atttaaaagg    3660
atctaggtga agatcctttt tgataatctc atgaccaaaa tcccttaacg tgagttttcg    3720
ttccactgag cgtcagaccc cgtagaaaag atcaaaggat cttcttgaga tccttttttt    3780
ctgcgcgtaa tctgctgctt gcaaacaaaa aaaccaccgc taccagcggt ggtttgtttg    3840
ccggatcaag agctaccaac tcttttccg aaggtaactg gcttcagcag agcgcagata    3900
ccaaatactt tccttctagt gtagccgtag ttaggccacc acttcaagaa ctctgtagca    3960
ccgcctacat acctcgctct gctaatcctg ttaccagtgg ctgctgccag tggcgataag    4020
```

| | |
|---|---:|
| tcgtgtctta ccgggttgga ctcaagacga tagttaccgg ataaggcgca gcggtcgggc | 4080 |
| tgaacggggg gttcgtgcac acagcccagc ttggagcgaa cgacctacac cgaactgaga | 4140 |
| tacctacagc gtgagctatg agaaagcgcc acgcttcccg aagggagaaa ggcggacagg | 4200 |
| tatccggtaa gcggcagggt cggaacagga gagcgcacga gggagcttcc agggggaaac | 4260 |
| gcctggtatc tttatagtcc tgtcgggttt cgccacctct gacttgagcg tcgattttg | 4320 |
| tgatgctcgt caggggggcg gagcctatgg aaaaacgcca gcaacgcggc cttttacgg | 4380 |
| ttcctggcct tttgctggcc ttttgctcac atgttctt | 4418 |

<210> SEQ ID NO 17
<211> LENGTH: 4652
<212> TYPE: DNA
<213> ORGANISM: Artificial Sequence
<220> FEATURE:
<223> OTHER INFORMATION: DNA plasmas having encoding sequence for influenza consensus M2e-NP

<400> SEQUENCE: 17

| | |
|---|---:|
| gctgcttcgc gatgtacggg ccagatatac gcgttgacat tgattattga ctagttatta | 60 |
| atagtaatca attacggggt cattagttca tagcccatat atggagttcc gcgttacata | 120 |
| acttacggta aatggcccgc ctggctgacc gcccaacgac ccccgcccat tgacgtcaat | 180 |
| aatgacgtat gttcccatag taacgccaat agggactttc cattgacgtc aatgggtgga | 240 |
| gtatttacgg taaactgccc acttggcagt acatcaagtg tatcatatgc caagtacgcc | 300 |
| ccctattgac gtcaatgacg gtaaatggcc cgcctggcat tatgcccagt acatgacctt | 360 |
| atgggacttt cctacttggc agtacatcta cgtattagtc atcgctatta ccatggtgat | 420 |
| gcggttttgg cagtacatca atgggcgtgg atagcggttt gactcacggg gatttccaag | 480 |
| tctccacccc attgacgtca atgggagttt gttttggcac caaaatcaac gggactttcc | 540 |
| aaaatgtcgt aacaactccg ccccattgac gcaaatgggc ggtaggcgtg tacggtggga | 600 |
| ggtctatata agcagagctc tctggctaac tagagaaccc actgcttact ggcttatcga | 660 |
| aattaatacg actcactata gggagaccca agctggctag cgtttaaact taagcttggt | 720 |
| accgagctcg gatccactag tccagtgtgg tggaattcgc caccatggac tggacctgga | 780 |
| tcctgttcct ggtcgctgcc gccaccaggg tgcacagcag cctgctgacc gaggtggaga | 840 |
| ccccccacccg gaacgagtgg ggctgccggt gcagcgacag cagcgaccgg ggcaggaagc | 900 |
| ggagaagcgc cagccagggc accaagcgga gctacgagca gatggaaaca ggcggcgagc | 960 |
| ggcagaacgc caccgagatc cgggccagcg tgggcagaat ggtcggcggc atcggccggt | 1020 |
| tctacatcca gatgtgcacc gagctgaagc tgtccgacta cgagggccgg ctgatccaga | 1080 |
| acagcatcac catcgagcgg atggtgctgt ccgccttcga cgagcggcgg aacagatacc | 1140 |
| tggaagagca cccccagcgcc ggcaaggacc ccaagaaaac cggcggaccc atctaccggc | 1200 |
| ggagggacgg caagtgggtg cgggagctga tcctgtacga caaagaggaa atccggcgga | 1260 |
| tctggcggca ggccaacaac ggcgaggacg ccacagccgg cctgacccac ctgatgatct | 1320 |
| ggcacagcaa cctgaacgac gccacctacc agcggacaag ggctctggtc cggaccggca | 1380 |
| tggaccccccg gatgtgcagc ctgatgcagg gcagcacact gcccagaaga agcggagccg | 1440 |
| ctggcgcagc cgtgaagggc gtgggcacca tggtgatgga actgatccgg atgatcaagc | 1500 |
| ggggcatcaa cgaccggaat ttttggaggg gcgagaacgg caggcggacc cggatcgcct | 1560 |
| acgagcggat gtgcaacatc ctgaagggca agttccagac agccgcccag cgggccatga | 1620 |
| tggaccaggt ccgggagagc cggaaccccg gcaacgccga gatcgaggac ctgatcttcc | 1680 |

```
tggccagaag cgccctgatc ctgcggggca gcgtggccca caagagctgc ctgcccgcct    1740
gcgtgtacgg actggccgtg ccagcggct acgacttcga gcgggagggc tacagcctgg    1800
tcggcatcga ccccttccgg ctgctgcaga actcccaggt gttcagcctg atccggccca    1860
acgagaaccc cgcccacaag tcccagctgg tctggatggc ctgccacagc gccgccttcg    1920
aggatctgag agtgagcagc ttcatccggg gcaccagagt ggtgcccagg gccagctgt    1980
ccaccagggg cgtgcagatc gccagcaacg agaacatgga agccatggac agcaacaccc    2040
tggaactgcg gagccggtac tgggccatcc ggaccagaag cggcggcaac accaaccagc    2100
agcgggccag cgccggacag atcagcgtgc agcccacctt ctccgtgcag cggaacctgc    2160
ccttcgagag ggccaccatc atggccgcct tcaccggcaa caccgagggc cggaccagcg    2220
acatgcggac cgagatcatc aggatgatgg aaagcgccag gcccgaggac gtgagcttcc    2280
agggcagggg cgtgttcgag ctgtccgatg agaaggccac caaccccatc gtgcccagct    2340
tcgacatgaa caacgagggc agctacttct tcggcgacaa cgccgaggaa tacgacaact    2400
accccctacga cgtgcccgac tacgcctgat gagcggccgc tcgagtctag agggcccgtt    2460
taaacccgct gatcagcctc gactgtgcct tctagttgcc agccatctgt tgtttgcccc    2520
tcccccgtgc cttccttgac cctggaaggt gccactccca ctgtcctttc ctaataaaat    2580
gaggaaattg catcgcattg tctgagtagg tgtcattcta ttctggggg tggggtgggg    2640
caggacagca agggggagga ttgggaagac aatagcaggc atgctgggga tgcggtgggc    2700
tctatggctt ctactgggcg gttttatgga cagcaagcga accggaattg ccagctgggg    2760
cgccctctgg taaggttggg aagccctgca agtaaactg gatggctttc ttgccgccaa    2820
ggatctgatg gcgcagggga tcaagctctg atcaagagac aggatgagga tcgtttcgca    2880
tgattgaaca agatggattg cacgcaggtt ctccggccgc ttgggtggag aggctattcg    2940
gctatgactg ggcacaacag acaatcggct gctctgatgc cgccgtgttc cggctgtcag    3000
cgcaggggcg cccggttctt tttgtcaaga ccgacctgtc cggtgccctg aatgaactgc    3060
aagacgaggc agcgcggcta tcgtggctgg ccacgacggg cgttccttgc gcagctgtgc    3120
tcgacgttgt cactgaagcg ggaagggact ggctgctatt gggcgaagtg ccggggcagg    3180
atctcctgtc atctcacctt gctcctgccg agaaagtatc catcatggct gatgcaatgc    3240
ggcggctgca tacgcttgat ccggctacct gcccattcga ccaccaagcg aaacatcgca    3300
tcgagcgagc acgtactcgg atggaagccg gtcttgtcga tcaggatgat ctggacgaag    3360
agcatcaggg gctcgcgcca gccgaactgt tcgccaggct caaggcgagc atgcccgacg    3420
gcgaggatct cgtcgtgacc catggcgatg cctgcttgcc gaatatcatg gtggaaaatg    3480
gccgcttttc tggattcatc gactgtggcc ggctgggtgt ggcggaccgc tatcaggaca    3540
tagcgttggc tacccgtgat attgctgaag agcttggcgg cgaatgggct gaccgcttcc    3600
tcgtgcttta cggtatcgcc gctcccgatt cgcagcgcat cgccttctat cgccttcttg    3660
acgagttctt ctgaattatt aacgcttaca atttcctgat gcggtatttt ctccttacgc    3720
atctgtgcgg tatttcacac cgcatcaggt ggcactttc ggggaaatgt gcgcggaacc    3780
cctatttgtt tatttttcta aatacattca aatatgtatc cgctcatgag acaataaccc    3840
tgataaatgc ttcaataata gcacgtgcta aaacttcatt tttaatttaa aaggatctag    3900
gtgaagatcc ttttgataa tctcatgacc aaaatccctt aacgtgagtt tcgttccac    3960
tgagcgtcag accccgtaga aaagatcaaa ggatcttctt gagatccttt ttttctgcgc    4020
gtaatctgct gcttgcaaac aaaaaaacca ccgctaccag cggtggtttg tttgccggat    4080
```

```
caagagctac caactctttt tccgaaggta actggcttca gcagagcgca gataccaaat    4140
actgttcttc tagtgtagcc gtagttaggc caccacttca agaactctgt agcaccgcct    4200
acatacctcg ctctgctaat cctgttacca gtggctgctg ccagtggcga taagtcgtgt    4260
cttaccgggt tggactcaag acgatagtta ccggataagg cgcagcggtc gggctgaacg    4320
gggggttcgt gcacacagcc cagcttggag cgaacgacct acaccgaact gagataccta    4380
cagcgtgagc tatgagaaag cgccacgctt cccgaaggga gaaaggcgga caggtatccg    4440
gtaagcggca gggtcggaac aggagagcgc acgagggagc ttccaggggg aaacgcctgg    4500
tatctttata gtcctgtcgg gtttcgccac ctctgacttg agcgtcgatt tttgtgatgc    4560
tcgtcagggg ggcggagcct atggaaaaac gccagcaacg cggccttttt acggttcctg    4620 gcctttgct ggccttttgc tcacatgttc tt                                   4652
```